US010156501B2

(12) United States Patent
Baer et al.

(10) Patent No.: US 10,156,501 B2
(45) Date of Patent: Dec. 18, 2018

(54) AUTOMATED MICRODISSECTION INSTRUMENT FOR DETERMINING A LOCATION OF A LASER BEAM PROJECTION ON A WORKSURFACE AREA

(71) Applicant: LIFE TECHNOLOGIES CORPORATION, Carlsbad, CA (US)

(72) Inventors: Thomas M. Baer, Mountain View, CA (US); Michael G. Youngquist, Palo Alto, CA (US); Brian W. Donovan, San Jose, CA (US); Alan E. Wessel, Mountain View, CA (US); Norbert H. Leclerc, Heidelberg (DE); Michael A. Smith, San Jose, CA (US); Craig S. Barker, San Carlos, CA (US); George M. Dawson, Santa Clara, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/434,200

(22) Filed: Feb. 16, 2017

(65) Prior Publication Data
US 2017/0284907 A1 Oct. 5, 2017

Related U.S. Application Data

(62) Division of application No. 14/275,812, filed on May 12, 2014, which is a division of application No.
(Continued)

(51) Int. Cl.
*G01N 1/28* (2006.01)
*G01B 11/00* (2006.01)

(52) U.S. Cl.
CPC ......... *G01N 1/2813* (2013.01); *G01B 11/002* (2013.01); *G01N 2001/282* (2013.01);
(Continued)

(58) Field of Classification Search
CPC .......... G01N 1/2813; G01N 2001/282; G01N 2001/284; G01N 1/44; G01B 11/002;
(Continued)

(56) References Cited

U.S. PATENT DOCUMENTS 3,680,947 A 8/1972 Wanesky
3,705,769 A 12/1972 Johannsmeier
(Continued)

FOREIGN PATENT DOCUMENTS

CH 566015 8/1975
DE 1263339 3/1968
(Continued)

OTHER PUBLICATIONS

Allred et al., "Biological features of human premalignant breast disease," Disease of the Breast (Philadelphia, Lippicot Williams & Wilkins, 2000, 355-366.
(Continued)

*Primary Examiner* — Michael P Lapage

(57) ABSTRACT

Systems and methods for automated laser microdissection are disclosed including automatic slide detection, position detection of cutting and capture lasers, focus optimization for cutting and capture lasers, energy and duration optimization for cutting and capture lasers, inspection and second phase capture and/or ablation in a quality control station and tracking information for linking substrate carrier or output microdissected regions with input sample or slide.

4 Claims, 12 Drawing Sheets

Related U.S. Application Data

11/236,045, filed on Sep. 26, 2005, now Pat. No. 8,722,357.

(60) Provisional application No. 60/664,438, filed on Mar. 23, 2005, provisional application No. 60/613,038, filed on Sep. 25, 2004.

(52) U.S. Cl.
CPC ....... *G01N 2001/284* (2013.01); *Y10T 156/10* (2015.01); *Y10T 156/1054* (2015.01)

(58) Field of Classification Search
CPC ........ G02B 21/24; G02B 21/26; G02B 21/18; G02B 21/36; G02B 21/362; G02B 21/0096; Y10T 156/10; Y10T 156/1054
See application file for complete search history.

(56) References Cited

U.S. PATENT DOCUMENTS

| | | |
|---|---|---|
| 3,848,962 A | 11/1974 | Nelson |
| 4,210,384 A | 7/1980 | Meyer et al. |
| 4,303,866 A | 12/1981 | Porro et al. |
| 4,333,983 A | 6/1982 | Allen |
| 4,436,385 A | 3/1984 | Fischer et al. |
| 4,508,435 A | 4/1985 | Graham et al. |
| 4,509,834 A | 4/1985 | Hodgson |
| 4,538,885 A | 9/1985 | Graham et al. |
| 4,552,033 A | 11/1985 | Marzhauser |
| 4,600,282 A | 7/1986 | Yamamura et al. |
| 4,614,431 A | 9/1986 | Komeyama |
| 4,623,839 A | 11/1986 | Garretson et al. |
| 4,627,009 A | 12/1986 | Holmes et al. |
| 4,672,559 A | 6/1987 | Jansson et al. |
| 4,673,261 A | 6/1987 | Hunt et al. |
| 4,684,781 A | 8/1987 | Frish et al. |
| 4,702,565 A | 10/1987 | Schilling et al. |
| 4,731,530 A | 3/1988 | Mikan |
| 4,760,385 A | 7/1988 | Jansson et al. |
| 4,807,984 A | 2/1989 | Kurimura et al. |
| 4,824,229 A | 4/1989 | Narita et al. |
| 4,836,667 A | 6/1989 | Ozeki |
| 4,852,985 A | 8/1989 | Fujihara et al. |
| 4,856,873 A | 8/1989 | Kleinberg |
| 4,871,245 A | 10/1989 | Ishikawa et al. |
| 4,920,053 A | 4/1990 | Inoue et al. |
| 4,923,294 A | 5/1990 | Courtenay |
| 4,954,715 A | 9/1990 | Zold |
| 4,964,708 A | 10/1990 | Mason |
| 4,987,006 A | 1/1991 | Williams et al. |
| 4,992,660 A | 2/1991 | Kobayashi |
| 5,017,428 A | 5/1991 | Mecke et al. |
| 5,029,791 A | 7/1991 | Ceccon et al. |
| 5,037,207 A | 8/1991 | Tomei et al. |
| 5,057,689 A | 10/1991 | Nomura et al. |
| 5,077,620 A | 12/1991 | Mauro |
| 5,089,909 A | 2/1992 | Kleinberg |
| 5,103,338 A | 4/1992 | Crowley et al. |
| 5,126,877 A | 6/1992 | Biber |
| 5,143,552 A | 9/1992 | Moriyama |
| 5,162,941 A | 11/1992 | Favro et al. |
| 5,165,297 A | 11/1992 | Krueger |
| 5,173,802 A | 12/1992 | Heller |
| 5,225,326 A | 7/1993 | Bresser et al. |
| 5,253,110 A | 10/1993 | Ichihara et al. |
| 5,257,182 A | 10/1993 | Luck et al. |
| 5,262,891 A | 11/1993 | Nakasato |
| 5,263,384 A | 11/1993 | Suzuki |
| 5,280,384 A | 1/1994 | Shibasaki |
| 5,287,272 A | 2/1994 | Rutenberg et al. |
| 5,288,996 A | 2/1994 | Betzig et al. |
| 5,296,963 A | 3/1994 | Murakami et al. |
| 5,298,963 A | 3/1994 | Moriya et al. |
| 5,312,393 A | 5/1994 | Mastel |
| 5,323,009 A | 6/1994 | Harris |
| 5,337,178 A | 8/1994 | Kung et al. |
| 5,345,333 A | 9/1994 | Greenberg |
| 5,357,366 A | 10/1994 | Marchlenski |
| 5,359,417 A | 10/1994 | Muller et al. |
| 5,367,401 A | 11/1994 | Sauletis |
| 5,378,675 A | 1/1995 | Takeyama et al. |
| 5,386,112 A | 1/1995 | Dixon |
| 5,393,647 A | 2/1995 | Neukermans et al. |
| 5,403,735 A | 4/1995 | Maruhashi et al. |
| 5,403,970 A | 4/1995 | Aoki |
| 5,412,503 A | 5/1995 | Nederlof |
| 5,420,716 A | 5/1995 | Fukaya |
| 5,428,690 A | 6/1995 | Bacus et al. |
| 5,434,703 A | 7/1995 | Morizumi |
| 5,450,233 A | 9/1995 | Yamamoto et al. |
| 5,455,420 A | 10/1995 | Ho et al. |
| 5,465,375 A | 11/1995 | Thepaut et al. |
| 5,468,967 A | 11/1995 | Chan et al. |
| 5,471,260 A | 11/1995 | Luce et al. |
| 5,479,252 A | 12/1995 | Worster et al. |
| 5,487,117 A | 1/1996 | Burges et al. |
| 5,492,861 A | 2/1996 | Opower |
| 5,497,430 A | 3/1996 | Sadovnik et al. |
| 5,504,366 A | 4/1996 | Weiss et al. |
| 5,506,725 A | 4/1996 | Koike et al. |
| 5,510,615 A | 4/1996 | Ho et al. |
| 5,517,353 A | 5/1996 | Ikoh et al. |
| 5,532,128 A | 7/1996 | Eggers et al. |
| 5,532,476 A | 7/1996 | Mikan |
| 5,532,873 A | 7/1996 | Dixon |
| 5,535,052 A | 7/1996 | Swann |
| 5,536,941 A | 7/1996 | Jorgens |
| 5,537,863 A | 7/1996 | Swann |
| 5,552,928 A | 9/1996 | Furuhashi et al. |
| 5,556,790 A | 9/1996 | Pettit |
| 5,557,456 A | 9/1996 | Garner et al. |
| 5,558,329 A | 9/1996 | Liu |
| 5,559,329 A | 9/1996 | Joseph et al. |
| 5,578,832 A | 11/1996 | Trulson et al. |
| 5,587,748 A | 12/1996 | Luce et al. |
| 5,587,833 A | 12/1996 | Kamentsky |
| 5,598,888 A | 2/1997 | Sullivan et al. |
| 5,602,674 A | 2/1997 | Weissman et al. |
| 5,619,035 A | 4/1997 | Weiss et al. |
| 5,621,207 A | 4/1997 | O'Mara |
| 5,625,705 A | 4/1997 | Recht |
| 5,631,734 A | 5/1997 | Stern et al. |
| 5,638,206 A | 6/1997 | Sumiya et al. |
| 5,659,421 A | 8/1997 | Rahmel et al. |
| 5,707,801 A | 1/1998 | Bresser et al. |
| 5,713,803 A | 2/1998 | Oshima |
| 5,715,327 A | 2/1998 | Wilhelm et al. |
| 5,728,527 A | 3/1998 | Singer et al. |
| 5,734,735 A | 3/1998 | Coleman, Jr. |
| 5,740,269 A | 4/1998 | Oh et al. |
| 5,740,270 A | 4/1998 | Rutenberg et al. |
| 5,745,601 A | 4/1998 | Lee et al. |
| 5,751,839 A | 5/1998 | Drocourt et al. |
| 5,767,923 A | 6/1998 | Coleman, Jr. |
| 5,774,357 A | 6/1998 | Hoffberg et al. |
| 5,778,108 A | 7/1998 | Coleman, Jr. |
| 5,787,188 A | 7/1998 | Nelson et al. |
| 5,843,644 A | 12/1998 | Liotta et al. |
| 5,843,657 A | 12/1998 | Liotta et al. |
| 5,859,699 A | 1/1999 | Baer et al. |
| 5,867,610 A | 2/1999 | Lee |
| 5,870,493 A | 2/1999 | Vogl et al. |
| 5,875,108 A | 2/1999 | Hoffberg et al. |
| 5,889,880 A | 3/1999 | Doerrer et al. |
| 5,920,360 A | 7/1999 | Coleman, Jr. |
| 5,920,477 A | 7/1999 | Hoffberg et al. |
| 5,939,278 A | 8/1999 | Boon et al. |
| 5,959,697 A | 9/1999 | Coleman, Jr. |
| 5,978,497 A | 11/1999 | Lee et al. |
| 5,985,085 A | 11/1999 | Baer et al. |
| 5,987,158 A | 11/1999 | Meyer et al. |
| 5,998,129 A | 12/1999 | Schutze et al. |
| 5,999,634 A | 12/1999 | Abbott et al. |

(56) References Cited

U.S. PATENT DOCUMENTS

| | | | |
|---|---|---|---|
| 6,010,888 A | 1/2000 | Liotta et al. | |
| 6,031,232 A | 2/2000 | Cohenford et al. | |
| 6,040,139 A | 3/2000 | Bova et al. | |
| 6,058,322 A | 5/2000 | Nishikawa et al. | |
| 6,061,471 A | 5/2000 | Coleman, Jr. | |
| 6,100,051 A | 8/2000 | Goldstein et al. | |
| 6,133,943 A | 10/2000 | Needham | |
| 6,134,354 A | 10/2000 | Lee et al. | |
| 6,143,535 A | 11/2000 | Palsson | |
| 6,146,897 A | 11/2000 | Cohenford et al. | |
| 6,148,099 A | 11/2000 | Lee et al. | |
| 6,157,446 A | 12/2000 | Baer et al. | |
| 6,181,811 B1 | 1/2001 | Kuan et al. | |
| 6,184,973 B1 | 2/2001 | Baer et al. | |
| 6,204,030 B1 | 3/2001 | Liotta | |
| 6,215,892 B1 | 3/2001 | Douglass et al. | |
| 6,215,550 B1 | 4/2001 | Baer et al. | |
| 6,226,392 B1 | 5/2001 | Bacus et al. | |
| 6,229,568 B1 | 5/2001 | Kawaguchi et al. | |
| 6,240,209 B1 | 5/2001 | Wilcke | |
| 6,259,807 B1 | 7/2001 | Ravkin | |
| 6,316,234 B1 | 11/2001 | Bova | |
| 6,327,377 B1 | 12/2001 | Rutenberg et al. | |
| 6,335,980 B1 | 1/2002 | Armato, III et al. | |
| 6,337,926 B2 | 1/2002 | Takahashi et al. | |
| 6,420,132 B1 | 7/2002 | Bonner et al. | |
| 6,456,899 B1 | 9/2002 | Gleason et al. | |
| 6,469,779 B2 | 10/2002 | Baer et al. | |
| 6,495,195 B2 | 12/2002 | Baer et al. | |
| 6,512,576 B1 | 1/2003 | Baer et al. | |
| 6,528,248 B2 | 3/2003 | Lossing et al. | |
| 6,531,318 B1 | 3/2003 | Palmer-Toy et al. | |
| 6,569,639 B2 | 5/2003 | Liotta et al. | |
| 6,639,657 B2 | 10/2003 | Baer et al. | |
| 6,690,470 B1 * | 2/2004 | Baer | G01N 1/2813 356/417 |
| 6,697,149 B2 | 2/2004 | Baer et al. | |
| 6,750,964 B2 | 6/2004 | Levenson et al. | |
| 6,757,412 B1 | 6/2004 | Parsons et al. | |
| 6,858,007 B1 | 2/2005 | Akselrod et al. | |
| 6,867,038 B2 | 3/2005 | Liotta et al. | |
| 7,027,133 B2 | 4/2006 | Baer et al. | |
| 7,075,640 B2 | 7/2006 | Baer et al. | |
| 7,221,447 B2 | 5/2007 | Baer et al. | |
| 7,456,938 B2 | 11/2008 | Malekafzall | |
| 8,346,483 B2 | 1/2013 | Kil | |
| 8,715,955 B2 | 5/2014 | Donovan et al. | |
| 8,722,357 B2 | 5/2014 | Baer et al. | |
| 2001/0005586 A1 | 6/2001 | Palsson et al. | |
| 2001/0038449 A1 | 11/2001 | Baer et al. | |
| 2002/0001837 A1 | 1/2002 | Baer et al. | |
| 2002/0015949 A1 | 2/2002 | Erlander et al. | |
| 2002/0090122 A1 * | 7/2002 | Baer | G01N 1/2813 382/128 |
| 2002/0103512 A1 | 8/2002 | Echauz et al. | |
| 2002/0142412 A1 | 10/2002 | Ogawa et al. | |
| 2002/0177885 A1 * | 11/2002 | Eisfeld | G06K 9/00127 607/89 |
| 2003/0008322 A1 | 1/2003 | Bonner et al. | |
| 2003/0030801 A1 | 2/2003 | Levenson et al. | |
| 2003/0032082 A1 | 2/2003 | Leclerc | |
| 2003/0058430 A1 | 3/2003 | Baer et al. | |
| 2003/0219151 A1 | 11/2003 | Curry et al. | |
| 2004/0051880 A1 * | 3/2004 | Seko | G01B 11/002 356/614 |
| 2004/0052328 A1 | 3/2004 | Sabol et al. | |
| 2004/0063326 A1 | 4/2004 | Szlufcik et al. | |
| 2004/0076613 A1 | 4/2004 | Mazarakis et al. | |
| 2004/0080818 A1 * | 4/2004 | Olschewski | G02B 21/002 359/391 |
| 2004/0093166 A1 * | 5/2004 | Kil | G01N 1/06 702/19 |
| 2006/0087643 A1 | 4/2006 | Donovan et al. | |
| 2006/0134692 A1 | 6/2006 | Emmert-Buck et al. | |
| 2006/0172278 A1 | 8/2006 | Bonner et al. | |
| 2007/0066967 A1 * | 3/2007 | Sieckmann | G01N 1/2813 606/10 |
| 2009/0140169 A1 | 6/2009 | Niehren | |
| 2014/0335560 A1 | 11/2014 | Baer et al. | |

FOREIGN PATENT DOCUMENTS

| | | |
|---|---|---|
| DE | 19603996 | 8/1997 |
| DE | 19636074 | 3/1998 |
| EP | 0748439 | 7/1999 |
| WO | 1991/007683 | 5/1991 |
| WO | 1994/002646 | 2/1994 |
| WO | 1995/023960 | 9/1995 |
| WO | 1995/030919 | 11/1995 |
| WO | 1997/013838 | 4/1997 |
| WO | 1998/027543 | 6/1998 |
| WO | 1998/035216 | 8/1998 |
| WO | 1998/044446 | 10/1998 |
| WO | 1999/019341 | 4/1999 |
| WO | 1999/045094 | 9/1999 |
| WO | 2000/034756 | 6/2000 |
| WO | 2000/034757 | 6/2000 |
| WO | 2001/033190 | 5/2001 |
| WO | 2002/037159 | 5/2002 |
| WO | 2002/057746 | 7/2002 |
| WO | 2004/025569 | 3/2004 |

OTHER PUBLICATIONS

Anonymous, "ChromaVision" website product description including Rare Cell Detection in Tissue and Rare Cell Detection in Cytospin Prep, retrieval date Jun. 21, 2004.

Ashkin et al. "Internal cell manipulation using infrared laser traps," *Proceedings of the National Academy of Sciences,* vol. 86, 1989, 7914-7918.

Bonner et al. "Laser capture microdissection: Molecular analysis of tissue," *Science,* vol. 278, 1997, 1481-1483.

Bonner et al, "Lasers and Electro-Optics", Summaries of Papers Presented at the Conference on May 23-28, 1999, 398-399.

Darling et al., "Revertant mosaicism : partial correction of a germ-line mutation in COL17A1 by a frame-restoring mutation," *Journal of Clinical Investigation,* vol. 103, No. 10, May 15, 1999, 1371-1377.

Duke University, "Evaluation of Cervical Cytology", *AHCPR* publication No. 99-E010, Feb. 1999.

Emmert-Buck et al. "Laser Capture Microdissection," *Science,* vol. 274, No. 5289, Nov. 8, 1996, 998-1001.

Fend et al., "Immuno-LCM : Laser Capture Microdissection of Immunostained Frozen Sections for mRNA Analysis," *American Journal of Pathology,* vol. 154, No. 1, Jan. 1999, 61-66.

Friend, "Getting up close to cancer genes," printed in USA Today, Science section, Aug. 5, 1977, p. 40.

Frosini et al., "A modified fuzzy C-means algorithm for feature selection", *Peachfuzz 2000, 19th International Conference of the North American Fuzzy Information Processing Society,* Piscataway, NJ, USA, IEEE, ISBN: 0-7803-6274-8, 2000, 148-152.

Fukui et al. "Microdissection of plant chromosomes by argon-ion laser beam," *Theoretical & Applied Genetics,* vol. 84, No. 7-8, Sep. 1992, 787-791.

Goldstein et al. "Thermal modeling of laser capture microdissection," *Applied Optics,* vol. 37, No. 31, 1998, 7378-7391.

Grohs et al., "Automated Cervical Cancer Screening", *Publisher: : Igaku-Shoin Medical Publishers,* Chapter 23, 1994, 305-317.

Harlow, eds. Antibodies: A Laboratory Manual. (New York, Cold Spring Harbor, 1988), pp. iii-ix (Table of Contents).

Heng et al. "High-Resolution Mapping of Mammalian Genes by In-Situ Hybridization to Free Chromatin," *Proceedings of the National of Academy of Sciences,* vol. 89, No. 20, Oct. 15, 1992, 9509-9513.

Isenberg et al. "Cell surgery by laser micro-dissection: a preparative method," *Journal of Microscopy,* vol. 107, Part 1, May 1976, 19-24.

(56) References Cited

OTHER PUBLICATIONS

Jarkrans, "Algorithms for Cell Image Analysis in Cytology and Pathology", *Comprehensive Summaries of Uppsala Dissertations*, 1996.

Jeyendran, "Association of the in-vitro fertilizing capacity of human spermatozoa with sperm morphology as assessed by three classification systems," *Human Reproduction*, vol. 1, Issue 5, Aug. 1986, 305-308.

Jimenez et al., "Neuropeptide expression and processing as revealed by direct matrix-assisted laser desorption ionization mass spectrometry of single neurons," *Journal of Neurochemistry*, vol. 62, No. 1, Jan. 1994, 404-407.

Isenberg et al. "Cell surgery by laser micro-dissection: a preparative method," *Journal of Microscopy*, vol. 107, No. 1, May 1976, 19-24.

Jong-Min Park, et al., "Analysis of active feature selection in optic nerve data using labeled fuzzy C-means clustering", *2002 IEEE World Congress on Computational Intelligence. 2002 IEEE International Conference on Fuzzy Systems*, vol. 2, 2002, Piscataway, NJ, USA, IEEE, ISBN: 0-7803-7280-8., 2002, 1580-1585.

Koperski, "Interactive models for semantic labeling of satellite images", *Earth Observing SystemsVII,Proceedings of the SPIE*, vol. 4814, Sep. 2002, 423-434.

Kubo et al. "Early detection of Knudson's two-hits in preneoplastic renal cells of the Eker rat model by the laser microdissection procedure," *Cancer Research*, vol. 55, No. 5, 1995, 989-990.

Kuska, "New aim-and-shoot technique speeds up cell analysis," Journal of National Cancer Institute, vol. 88, No. 23, Dec. 4, 1996, 1708-1709.

LCM, Introduction to Laser Capture Microdissection, http://dir.nichd.nih.gov/lcm/LCM_Website_Introduction.htm, 1996-1997, 1-3.

LCM R&D Lab, http://dir.nichd.nih.gov/lcm/Text_for_RD_Core1.html#Computer%20control, 1997, p. 1-2 and 1-4.

Lawrence et al. "Sensitive High-Resolution Chromatin and Chromosome Mapping In-Situ: Presence and Orientation of Two Closely Integrated Copies of EBV in a Lymphoma Line," *Cell*, vol. 52, No. 1, Jan. 15, 1988, 51-61.

Lewis, "Laser aids Alzheimer's study," *Biophotonics International*, Nov./Dec. 1998, 1-2.

Lichter et al. "High-Resolution Mapping of Human Chromosome 11 by In-Situ Hybridization with Cosmid Clones," *Science*, vol. 247, No. 4938, Jan. 5, 1990, 64-69.

Manuelidis et al. "High-Resolution Mapping of Satellite DNA Using Biotin-Labeled DNA Probes," Journal of Cell Biology, vol. 95, No. 2, Part 1, Nov. 1982, 619-625.

Meier-Ruge et al. "The laser in the Lowry technique for microdissection of freeze-dried tissue slices," *Histochemical Journal*, vol. 8, No. 5, Jul. 1976, 387-401.

Morruzzi et al., "Quantification and classification of human sperm morphology by computer assisted image analysis", *Fertility and Sterility*, vol. 50, Issue 1, Jul. 1998, 142-152.

Perez-Sanchez, "Morphometric Analysis of human sperm morphology", *International Journal of Andralogy*, vol. 17, No. 5, Oct. 1994, 248-255.

Petrosian et al., "Computer-Aided Diagnosis in Mammography: Classification of Mass and Normal Tissue by Texture Analysis", *Physics of Medicine & Biology*, vol. 39, No. 12, Dec. 1994, 2273-2288.

Pizzi, "Diagnostic Cytology Learning Page", http://www-ocs.colorado.edu/-metzy/pizzia/learning.sub.--page.html, Written Feb. 4, 1997, Last updated Aug. 4, 1998, 1998.

Rangayyan et al., "Measures of Acutance and Shape for Classification of Breast Tumors", *IEEE Transactions on Medical Imaging*, vol. 16, No. 6, Dec. 1997, 799-810.

Sahiner et al., "Improvement of Mammographic Mass Characterization Using Spiculation Measures and Morphological Features", *Medical Physics*, vol. 28, No. 7, Jul. 2001, 1455-1465.

Salomie et al., "Multivariate Techniques for Medical Image Segmentation", http://www.etro.vub.ac.beimembersideklerck.rudi/redimedia/segmentation/se-gment.htm, 2001.

Schachter et al., "Some Experiments in Image Segmentation by Clustering of Local Feature Values", *Pattern Recognition*, vol. 11, No. 1, 1979, 19-28.

Schindler et al. "Automated analysis and survival selection of anchorage-dependent cells under normal growth conditions," *Cytometry*, vol. 6, No. 4, Jul. 1985, 368-374.

Schindler et al. "Select, microdissect & eject," *Nature Biotechnology*, vol. 16, No. 8, Aug. 1998, 719-720.

Schultze, "Identification of expressed genes by laser-mediated manipulation of single cells," *Nature Biotechnology*, vol. 16, No. 8, Aug. 1998, 737-742.

Simone et al. "Laser capture microdissection: Opening the microscopic frontier to molecular analysis," *Trends Genetics*, vol. 14, No. 7, Jul. 1998, 272-276.

Srinivasan, "Ablation of polymers and biological tissue by ultraviolet lasers", *Science*, vol. 234, 1986, 559-565.

Suarez-Quian et al., "Laser Capture Microdissection of Single Cells from Complex Tissues," BioTechniques, vol. 26, No. 2, Feb. 1999, 328-335.

UCSD Cancer Center, http://cancer.ucsd.edu/molpath/examples.asp. And also see http://cancer .ucsd.edu/molpath/introduce.asp (retrieved from U.S. Appl. No. 10/011,515 892 dated Mar. 10, 2004).

Van Den Engh et al. "Estimating Genomic Distance from DNA Sequence Location in Cell Nuclei by a Random Walk Model," Science vol. 257, No. 5075, Sep. 4, 1992, 1410-1412.

Veigel et al. "New cell biological applications of the laser microbeam technique: the microdissection and skinning of muscle fibers and the perforation and fusion of sarcolemma vesicles," *European Journal of Cell Biology*, vol. 63, No. 1, Feb. 1994, 140-148.

\* cited by examiner

AUTOMATED MICRODISSECTION INSTRUMENT FOR DETERMINING A LOCATION OF A LASER BEAM PROJECTION ON A WORKSURFACE AREA

CROSS-REFERENCE TO RELATED APPLICATIONS

This application is a division of U.S. patent application Ser. No. 14/275,812, filed May 12, 2014, which is a division of U.S. patent application Ser. No. 11/236,045, filed Sep. 26, 2005, which claims priority to U.S. Provisional Patent Application No. 60/664,438, filed Mar. 23, 2005, and to U.S. Provisional Patent Application No. 60/613,038, filed Sep. 25, 2004, all of which are incorporated herein by reference in their entirety.

FIELD OF THE INVENTION

The invention relates generally to the field of laser microdissection. More particularly, the invention relates to an automated laser microdissection instrument.

BACKGROUND

Tissue biopsies are frequently obtained for diagnostic and therapeutic purposes. Typically a tissue biopsy sample consists of a 5 to 10 micron slice of tissue that is placed on a glass microscope slide using techniques well known in the field of pathology. The tissue sample will typically consist of a variety of different types of cells. Often a pathologist will desire to remove only a small portion of the tissue for further analysis. Before the advent of laser microdissection, pathologists would have to resort to various time-consuming and imprecise microdissection techniques to obtain a sample of the desired region of a biopsy. Laser microdissection provides a simple method for the procurement of selected human cells from a heterogeneous population contained on a typical histopathology biopsy slide. The laser microdissection technique is generally described in the published article: Laser Capture Microdissection, Science, Volume 274, Number 5289, Issue 8, pp 998-1001, published in 1996, incorporated herein by reference, and in the following U.S. Pat. Nos. 5,859,699; 5,985,085; 6,184,973; 6,157,446; 6,215,550; 6,459,779; 6,495,195; 6,512,576; 6,528,248 all herein incorporated by reference in their entirety.

Laser microdissection systems generally comprise an inverted microscope fitted with a laser. Tissue samples are mounted, typically on a standard glass slide, and a transparent thermoplastic transfer film is placed over the tissue section. This film is often manufactured containing organic dyes that are chosen to selectively absorb in the near infrared region of the spectrum overlapping the emission region of common AlGaAs laser diodes. When the film is exposed to the focused laser beam the exposed region is heated by the laser and melts, adhering to the tissue in the region that was exposed.

The laser melts the film in precise locations which serves to bind the film to a targeted cell or cells. Individual cells or clusters of cells can be targeted by the laser, depending on the diameter of light emitted from the laser. Heat generated by the laser is dissipated by the film, thus limiting the damage done to the targeted cells and the components therein. After the targeted cells are bound to the film, they are removed from the sample. The targeted cells are then extracted for further analysis. The transfer film can be mounted on a transparent cap that fits on a microcentrifuge tube to facilitate extraction.

The following invention is a new method and apparatus for laser microdissection that solves a number of problems of conventional laser microdissection.

BRIEF SUMMARY OF THE INVENTION

In accordance with one aspect of the invention, there is provided a method for laser microdissection. The method includes the step of providing a layer of biological material that is applied to the surface of a first substrate. A polymer layer is provided. At least one targeted portion of biological material located on the first substrate is identified. The polymer layer is placed in juxtaposition with the first substrate on the side of the biological material in the location of the at least one targeted portion of biological material. A laser source is provided and activated so as to describe at least one closed or substantially closed path around the at least one targeted portion of biological material or directly at the least one targeted portion of biological material. At least one portion of biological material is transferred from the layer of biological material to the polymer layer. The polymer layer is moved to a quality control station. At least one portion of biological material that is present on the polymer layer while the polymer layer is located in the quality control station is further identified. The at least one laser source may be activated and directed at the at least one portion of identified biological material that is present on the polymer layer while the polymer layer is located in the quality control station.

In accordance with another aspect of the invention, there is provided a method for automatically determining the location of a laser beam projection on a worksurface area of a laser microdissection instrument that is operatively coupled to a microprocessing device and a digital image acquisition system containing a digital image sensor. The method may include the step of increasing the intensity of the laser beam. In another variation, the method includes emitting laser light at a level sufficient to be detected by the digital image sensor. The increased light intensity of the laser beam is detected by the digital image sensor. The pixel location of the increased light intensity on the digital image sensor is determined and converted to a coordinate location corresponding to the worksurface area. The coordinate location is assigned as the location of the laser beam from which laser cutting or capture operations proceed.

In accordance with another aspect of the invention, there is provided a method for optimizing the focus of a laser beam in a laser microdissection instrument. The method includes the step of providing a laser microdissection instrument having a worksurface. A first laser source and laser focusing lens is disposed on a first side of the worksurface. An objective lens and image acquisition system is disposed on a second side of the worksurface. A sample is placed on the worksurface. The objective lens is focused on the sample for a clear image of the sample acquired by the image acquisition system. The first laser source is activated to emit a laser beam directed at the sample. The laser beam from the first laser source is focused by moving the laser focusing lens. The objective lens is re-focused on the sample by moving the objective lens a distance. The laser beam from the first laser source is kept at the desired focus by moving the focusing lens by substantially the same distance that the objective lens was moved when re-focused.

In accordance with yet another aspect of the invention, there is provided a method for a laser microdissection instrument. The method includes the step of providing a first substrate having a transfer film attached. At least one second substrate having biological material is also provided. The second substrate with the biological material is introduced into the laser microdissection instrument. At least one targeted portion of biological material on the second substrate is identified. The first substrate is placed in juxtaposition with the second substrate on the side of the biological material in the location of the at least one targeted portion of biological material. A first laser source is provided and activated to adhere at least one region of the transfer film to at least one portion of biological material. At least one portion of biological material is transferred from the second substrate to the first substrate. At least one tracking information is recorded and associated with the first substrate.

In accordance with another aspect of the invention, there is provided a digital microscope for observing a sample. The digital microscope includes a worksurface for receiving a sample. The worksurface intersects a primary optical axis of the microscope. A substrate-receiving location is provided on the worksurface for receiving a sample-bearing substrate. The worksurface includes a first opening in the substrate-receiving location for alignment with the primary optical axis to permit pathing of light through the first opening in the worksurface. The digital microscope includes a digital image acquisition system that includes an image sensor configured to automatically detect the presence of the substrate in the substrate-receiving location.

BRIEF DESCRIPTION OF THE DRAWINGS

The foregoing and other advantages of the invention will become apparent upon reading the following detailed description and upon reference to the drawings in which.

Figure 1:
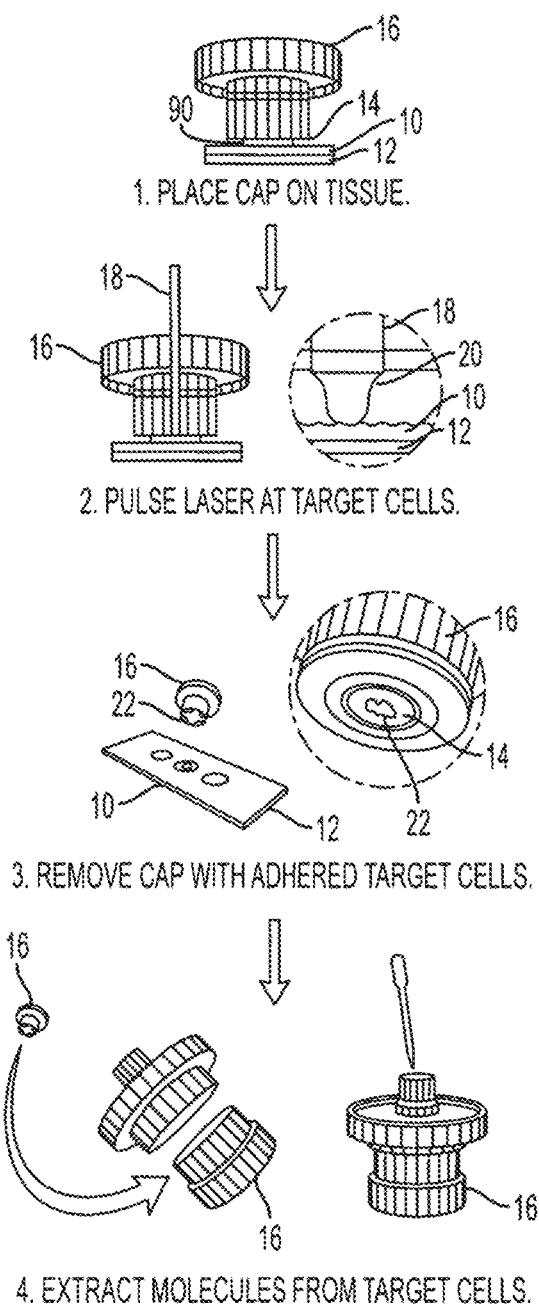
FIG. 1 is a depiction of a laser microdissection process shown in four steps according to the invention.

While the invention is susceptible to various modifications and alternative forms, specific variations have been shown by way of example in the drawings and will be described herein. However, it should be understood that the invention is not limited to the particular forms disclosed. Rather, the invention is to cover all modifications, equivalents, and alternatives falling within the spirit and scope of the invention as defined by the appended claims.

DETAILED DESCRIPTION OF THE INVENTION

The invention and the various features and advantageous details thereof are explained more fully with reference to the nonlimiting embodiments that are illustrated in the accompanying drawings and detailed in the following description. Descriptions of well known components and processing techniques are omitted so as not to unnecessarily obscure the invention in detail.

The entire contents of U.S. Pat. No. 6,469,779 filed Feb. 4, 1998, entitled "Laser Capture Microdissection Device"; U.S. Pat. No. 5,859,699, filed Feb. 7, 1997; U.S. Pat. No. 6,495,195, filed Feb. 14, 1997; and U.S. Pat. No. 5,985,085, filed Dec. 4, 1997 are hereby expressly incorporated by reference into the present application as if fully set forth herein.

With reference to FIG. 1, a laser microdissection device operates to carry out the following general steps. A tissue 10 or smear fixed on a standard microscope slide 12 by routine protocols is introduced into a laser microdissection instrument. A polymer film or transfer film 14 is provided which is typically affixed to a solid substrate forming a carrier 16. The carrier 16 can be of any shape. One shape for the carrier is a cap for conveniently introducing a sample into a vessel, such as a microcentrifuge tube, and sealing the vessel. The words "cap" and "carrier" are used interchangeably and it is understood by one skilled in the art that the carrier can be of any shape even where the term "cap" is employed.

The tissue sample 10 mounted on a substrate surface is placed adjacent a transfer film carrier cap 16 which further ensures that transfer film 14 stays out of contact with the tissue 10 at this stage as shown in step one of FIG. 1. Alternatively, the transfer film carrier 16 can be placed in contact with the tissue 10. Upon visualizing the tissue 10 by a microscope, a user may select a region for microdissection. The selected section of the tissue is captured by pulsing at least one region of the transfer film with a low power infrared laser emitting a laser beam 18 which activates the transfer film 14 which then expands down into contact with the tissue 10 as shown in step two of FIG. 1. The at least one activated region 20 of the transfer film 14 adheres to the at least one identified portion of desired cell(s) 22 of the tissue sample. Microdissection is completed by lifting the transfer film carrier 16, with the desired cell(s) 22 attached to the transfer film 14 surface while the surrounding tissue remains intact as shown in step three of FIG. 1. Extraction and subsequent molecular analysis of the cell contents, DNA, RNA or protein, are then carried out by employing devices and standard methods as shown in step four of FIG. 1 and described in U.S. application Ser. No. 09/844,187 entitled "Laser capture microdissection (LCM) extraction device and device carrier and method for LCM fluid processing" incorporated herein by reference in its entirety.

Laser microdissection employs a polymer transfer film that is placed in juxtaposition to the tissue sample. The transfer film may or may not contact the tissue sample. This transfer film is typically a thermoplastic manufactured containing organic dyes that are chosen to selectively absorb in the near infrared region of the spectrum overlapping the emission region of common AlGaAs infrared laser diodes. When the film is exposed to the focused laser beam the exposed region is heated by the laser and melts, adhering to the tissue in the region that was exposed. The film is then lifted from the tissue and the selected portion of the tissue is removed with the film. Thermoplastic transfer films such as a 100 micron thick ethyl vinyl acetate (EVA) film available from Electroseal Corporation of Pompton Lakes, N.J. (type E540) have been used in LCM applications. The film is chosen due to its low melting point of about 90° C.

Figure 2:
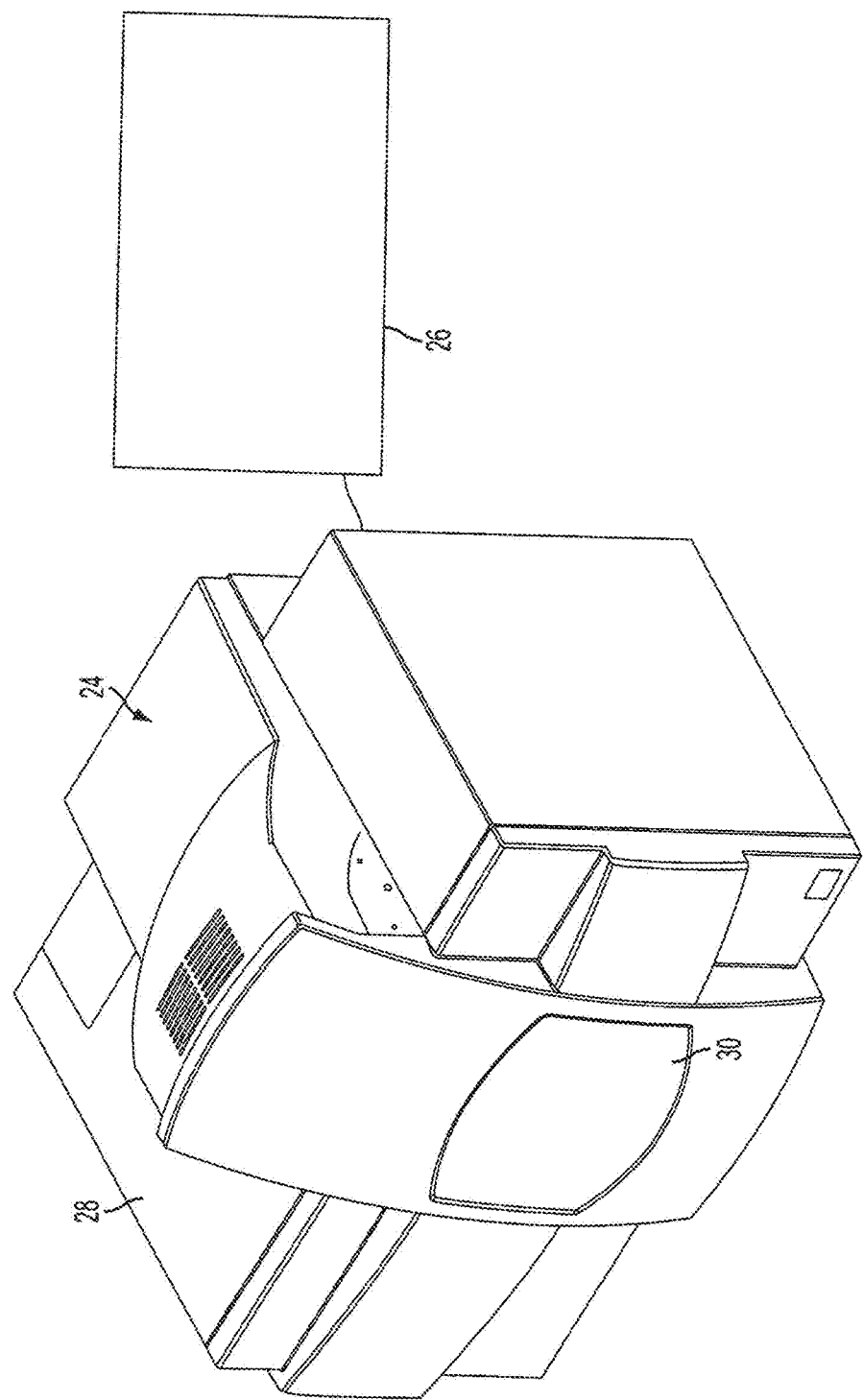
FIG. 2 is a perspective view of the laser microdissection instrument connected to a computer and display according to the invention.

With reference to FIG. 2, a laser microdissection instrument 24 is shown connected to a computer 26 with a hard drive and an LCD monitor 27. The computer 26 includes the Windows operating system and basic Windows applications and is loaded with appropriate software to control instrument operation. The computer receives input from the user and controls the operation of the laser microdissection instrument 24. The laser microdissection instrument components are secured within a housing 28 that includes an automated sliding door 30 for accessing the instrument and inserting and removing tissue samples, slides and transfer film carriers.

Figure 3:
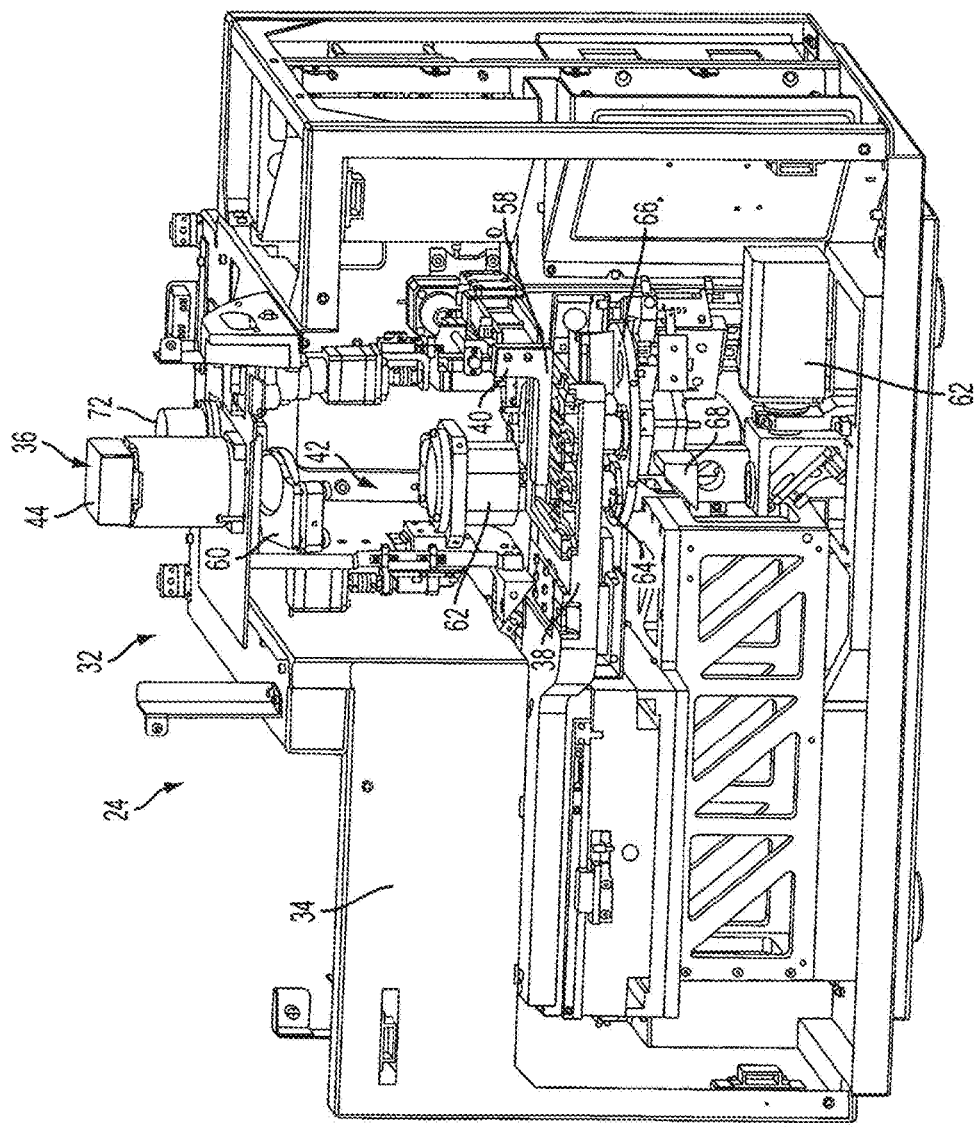
FIG. 3 is a perspective view of the laser microdissection instrument without the housing according to the invention.

Referring now to FIG. 3, there is shown the laser microdissection instrument 24 with the housing 28 removed. The laser microdissection instrument 24 includes a microscope 32 mounted on an assembly frame 34. The microscope 32 includes an illumination system 36, a worksurface 38, a handling system 40 and an optical system 42. The microscope frame 34 carries the components of the microscope 32. The illumination system 36 comprises a white light illuminator 44 and a condenser 62 mounted on the frame 34. The illumination system 36, worksurface 38 and optical system 42 are arranged in an inverted transmitted-light microscope fashion such that the illumination system is arranged above the worksurface 38 and at least one objective is arranged below the worksurface 38.

The worksurface 38 is also mounted on the instrument frame 34 and is adapted for receiving one or more specimens and transmitting light therethrough. A vacuum chuck may also be included to secure the specimen mounted on a specimen holder in position. The worksurface 38 operates as a translation stage and is automatically or manually movable in all directions, in particular, the planar X-Y directions. The automated translation stage includes a lateral translation motor and a fore-and-aft translation motor to allow complete manipulation in the X-Y plane. The motors are controlled by a controller connected to the computer which receives input such as via a mouse cursor. A mouse cursor can be used by an operator to trace a path on a visual display unit depicting a live or static image of the specimen to effect movement of the worksurface. A sophisticated road-map imaging system for navigating the specimen is described in U.S. Patent Publication No. 2002-0090122 which is incorporated herein by reference in its entirety.

Figure 4:
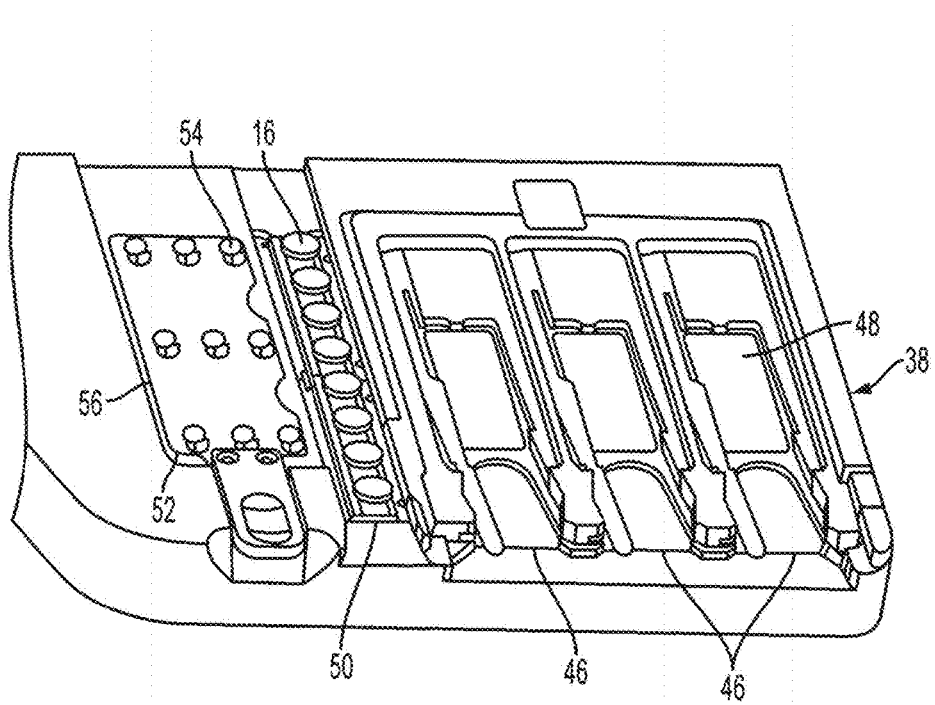
FIG. 4 is a perspective view of the worksurface of the laser microdissection instrument according to the invention.

With particular reference to FIG. 4, there is shown the worksurface 38. The worksurface 38 includes slide locations 46 for handling multiple tissue samples simultaneously. Although three slide locations 46 are depicted, the invention is not so limited and any number of slide locations is within the scope of the present invention. Each slide location 46 is designed to receive a substrate surface bearing sample tissue for microdissection. In the embodiment depicted in FIG. 4, the substrate surface to be received within the slide locations 46 is a standard microscope slide. Accordingly, the slide locations are appropriately dimensioned although the invention is not so limited and any type and style of substrate surface may be adapted to fit a customized worksurface. Each slide location 46 includes at least one opening 48 in the worksurface 38. The worksurface 38 further includes a staging area 50 for receiving transfer film carriers 16 or cap cassettes. The worksurface 38 also includes an unload station 52 for unloading caps from the slide locations 46 after microdissection. The unload station 52 includes an unload slot 56 for receiving an unload tray onto which caps are placed. The worksurface 38 also includes a quality control station 54. The quality control station 54 includes an opening (not shown) in the worksurface 38 that permits illumination and laser light to pass. The quality control station 54 is designed for viewing the cap following cell capture, generating an image of the cap, and/or further ablating portions of the collected sample residing on the cap after cell capture. These features of the invention will be discussed in greater detail below.

The handling system 40 is connected to the frame 34 and comprises a lift fork 58. The lift fork 58 is moved in and out of the work surface by a translation motor and a lift motor operates to move the lift fork vertically. The lift fork is adapted to pick a carrier located at a staging or supply area of the worksurface and place the carrier in juxtaposition with the tissue specimen located in one of the slide locations 46. When microdissection is completed, the lift fork is adapted to pick the carrier from juxtaposition with the specimen and place it in the unload station 52 and/or quality control station 54 where the carrier may further cap an analysis vessel. The handling system also includes a visualizer filter. The visualizer filter is a piece of diffuser glass positioned above tissue sample. The light from above is diffused by the visualizer filter illuminating the sample from all angles. The visualizer filter can be moved in and out of position and is located on the lift fork. The automated handling system is described in detail in U.S. Pat. No. 6,690,470 to Baer et al. and is incorporated herein by reference in its entirety.

The optical system 30 of the microscope includes several optical elements known to a person skilled in the art to make a microscope and laser microdissection instrument operate properly. These elements, mounted on the instrument frame, are combined to create an optical train of optical elements for pathing light. The optical system includes but is not limited to the following optical elements: mirror(s), dichroic mirror(s), lens(es), objective, beam-diameter adjuster, cut-off filter, diffuser, condenser, eyepiece and image acquisition system such as a camera.

The optical system together with its optical elements is arranged such that white light from the illumination system 36 passes down toward the worksurface 38. The white light passes a dichroic mirror 60 and a focusing condenser lens 62. The white light passes through one of the openings in the worksurface 38 along a primary optical axis and enters an objective 64 located beneath the worksurface 38. Multiple objectives are located on an objective turret wheel 66 which is automatically controlled by the computer. White light from the objective 64 is then reflected by one or more mirrors 68 to an eyepiece (not shown) and/or a camera or image acquisition system 70. The live image captured by the image acquisition system 70 is transmitted to the computer and displayed on a visual display unit in a software application window for the live video. Static images may also be captured by the image acquisition system and displayed side-by-side with the live video on the visual display unit in a software application window for the static roadmap image. A cut-off filter may be located between the objective and the image acquisition system or eyepiece. A diffuser and a beam diameter adjuster (not shown) may also be incorporated in the optical train and located between the dichroic mirror and the translation stage. A series of microscope objectives may be selectably deployed from an objective turret wheel 66 which is controlled by an objective wheel motor while a second objective focus motor operates to automatically adjust the foci of objectives which have been positioned. One skilled in the art will understand that the optical elements may be arranged in various ways for optimum performance.

Connected to the microscope and mounted on the instrument frame 34 is capture laser source 72. The capture laser source is typically an infrared (IR) laser source such as a AlGaAs laser diode having a wavelength of approximately 810 nanometers. The laser diode with collimating optics emits a beam of IR laser light that is incident upon the dichroic mirror 60. The capture or infrared laser beam enters the optical train at the dichroic mirror 60 and is reflected downward through the focusing condenser lens 62 and/or beam diameter adjuster toward the worksurface 38. Simultaneously, the dichroic mirror 60 allows white light from the illumination system 36 to also pass toward worksurface resulting in the IR laser beam and the white light illumination being superimposed along the primary optical axis. A laser focus motor which is connected to the controller and computer operates to control the focusing lens 62 and adjust the IR laser beam spot size. The computer 26 also delivers signals to the IR laser via the controller to initiate IR laser pulses, adjust beam size and control IR laser power.

The capture laser 72 operates in two modes, idle mode and pulse mode. In idle mode, the IR laser beam path provides a visible low amplitude signal that can be detected via the image acquisition system 70 when a visual alignment of the laser spot with a portion of tissue is desired. In pulse mode, the 1R laser beam path delivers energy for microdissection and the optical characteristics of a cut-off filter attenuate the IR laser beam path sufficiently such that substantially none of the energy from the IR laser beam exits through the microscope.

Suitable capture laser pulse widths are from 0 to approximately 1 second, preferably from 0 to approximately 100 milliseconds, more preferably approximately 50 milliseconds. In one variation, the spot size of the laser at the transfer film is variable from approximately 1.0 to 100 microns, from 1 to 60 microns, or from 5 to 30 microns. From the standpoint of the clinical operator, the widest spot size range is the most versatile. A lower end point in the spot size range on the order of 5 microns is useful for transferring single cells.

Suitable lasers can be selected from a wide power range. For example, a 100 milliwatt laser can be used. On the other hand, a 50 mW laser can be used. The laser can be connected to the rest of the optical subsystem with a fiber optical coupling. Smaller spot sizes are obtainable using diffraction limited laser diodes and/or single mode fiber optics. Single mode fiber allows a diffraction limited beam.

While the capture laser diode can be run in a standard mode such as $TEM_{00}$, other intensity profiles can be used for different types of applications. Further, the beam diameter could be changed with a stepped lens (not shown) placed in the lens assembly. Changing the beam diameter permits the size of the portion of the transfer film that is activated to be adjusted. Given a tightly focused initial condition, the beam size can be increased by defocusing. Given a defocused initial condition, the beam size can be decreased by focusing. The change in focus can be in fixed amounts. Furthermore, the change in focus can be obtained by means of indents on a movable lens mounting and/or by means of optical glass steps. In any event, increasing or decreasing the optical path length is the effect that is needed to alter the focus of the beam, thereby altering the spot size. For example, inserting a stepped glass prism into the beam so the beam strikes one step tread will change the optical path length and alter the spot size.

Figure 5:
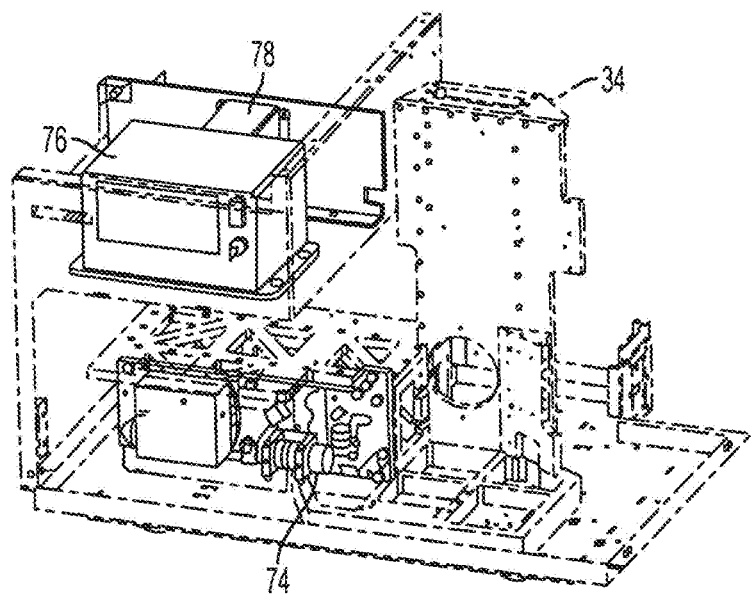
FIG. 5 is a front perspective view of the cutting laser components mounted on the frame of the laser microdissection instrument according to the invention.

Referring now to FIG. 5, there is shown a front perspective view of a cutting laser source 74 in addition to related and interconnected cutting laser components such as a cutting laser power supply 76 and air channel 78 installed onto the frame 34 of the instrument 24 of FIG. 3. While FIG. 3 does not show the cutting laser source 74, it is to be understood that the cutting laser and its components are integrated into the instrument 24 of FIG. 3 in the manner shown in FIG. 5 and that FIG. 5 shows only the detail of the cutting laser components with other instrument components removed for clarity.

The cutting laser source 74 is connected to the microscope and it is typically an ultraviolet (UV) laser source 74. The UV laser source emits a beam of laser light that is reflected by one or more mirrors and directed into the primary optical axis. The UV laser light enters the optical train and is reflected upward through the objective lens 64. The objective 64 focuses and adjusts the UV laser beam diameter. The UV laser beam then travels toward the worksurface 38 and through one of the openings in the worksurface and at a tissue sample residing on a slide located in the slide location 46 or at a captured tissue sample located on a cap in the quality control station 54. It is understood that the worksurface 38 is automatically moved to align particular openings in the worksurface with the optical paths of the lasers or primary optical axis for the intended operation. Simultaneously, the dichroic mirror 60 allows white light from the illumination system to also pass toward the worksurface 38 resulting in the UV laser beam and the white light illumination being superimposed along the primary optical axis. Alternatively, the UV laser can be positioned above the worksurface 38 and directed through the focusing lens 62 along the primary axis and toward the specimen resting on the worksurface 38. The computer 26 also delivers signals to the cutting UV laser via the controller to initiate UV laser pulses, change beam diameter and control cutting UV laser power. UV laser pulse widths and beam diameter can be changed in the same manner as described above with respect to the IR laser source.

Figure 6:
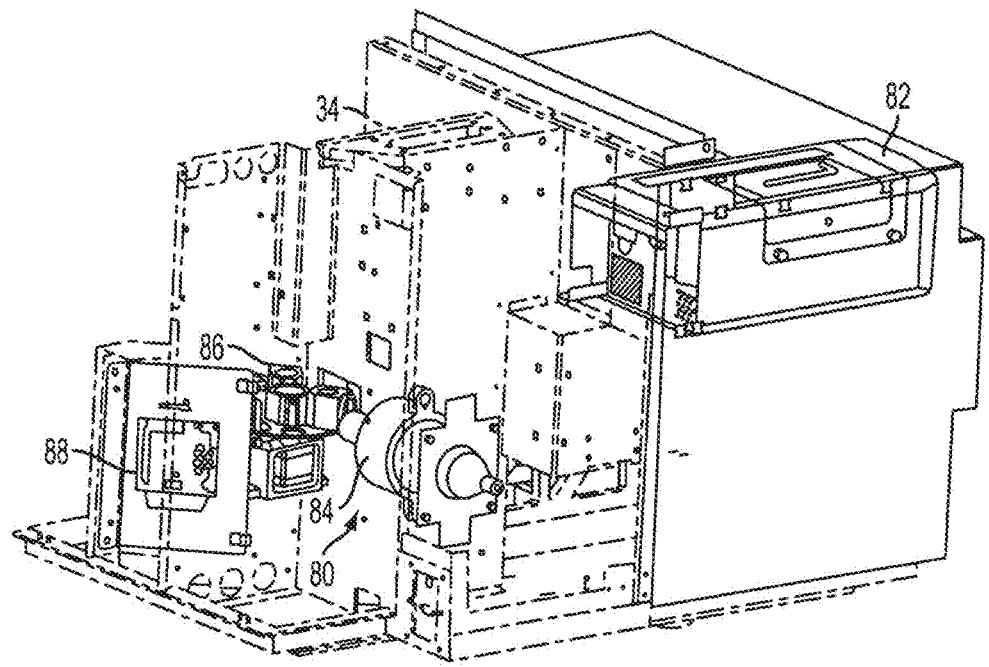
FIG. 6 is a rear perspective view of the fluorescence system mounted on the frame of the laser microdissection instrument according to the invention.

Focusing now on FIG. 6, there is shown a rear perspective view of a fluorescence system 80 connected to the frame 34 of the instrument 24. FIG. 6 displays the related and interconnected components of the fluorescence system 80 such as the power supply and light source 82, EPI fluorescence illuminator 84, filter wheel 86 and controller 88 installed onto the frame 34 of the instrument 24 of FIG. 3. While FIG. 3 does not show the fluorescence system 80, it is to be understood that the fluorescence system is integrated with the instrument 24 in the manner shown in FIG. 6 in addition to the components shown in FIG. 3 and optionally with the components of FIG. 5 and that FIG. 6 shows only the detail of the fluorescence system with other instrument components removed for clarity purposes only.

The fluorescence system 80 is adapted for automated selection of cells or specific regions of a sample for microdissection using fluorescently-stained tissue samples. In image analysis, the fluorescently-labeled tissue is placed in a microdissection instrument and with the fluorescent system, the cells are detected through an analysis of the image formed by the microscope. Image analysis is known in the art and is also described in detail in WO 2004/025569 which is herein incorporated by reference in its entirety.

The fluorescence system 80 includes a fluorescence excitation light source, for example, a xenon or mercury lamp, which emits a specific wavelength or wavelength range. The specific wavelength or wavelength range of a beam emitted by the light source is selected by a fluorescence filter wheel 86 operated by a fluorescence filter changer motor, to excite a fluorescent system (chemical markers and optical filtering techniques that are known in the industry) that is incorporated in or applied to the sample to be microdissected. The wavelength range transmitted from the excitation light source can be selected. The sample includes at least one member selected from the group consisting of chromophores and fluorescent dyes (synthetic or organic), and the process of operating the instrument includes identifying at least a portion of the sample with light that excites at least one member, before the step of transferring a portion of the sample to the laser microdissection transfer film. The fluorescent beam can be made coincident or coaxial with both the IR/UV laser beam path and the white light from illuminator path. Fluorescence emitted by the sample is amplified by an objective changer 66, reflected by a camera changer mirror and captured for live viewing by the acquisition system 70 which comprises a camera. A filter wheel 86 motor operates to adjust the fluorescent beam and the emitted fluorescent beam. Optionally the objective changer may be implemented in the form of a wheel to accommodate a multiplicity of objectives (five objectives, as depicted) for providing different amplifications of the fluorescent image for the camera. A more detailed exposition of automated fluorescent laser microdissection is found in U.S. Pat. No. 6,690,470 which is incorporated herein by reference in its entirety.

Referring back to FIGS. 1-6, a sample of biological material 10 to be microdissected is applied to a substrate such as a glass slide 12 using routine protocols. The substrate with the sample affixed thereto is inserted into the laser microdissection instrument 24 through automatic door 30 and inserted into a slide opening 48 located on the worksurface 38. The instrument 24 automatically detects the presence of a slide 12 when a slide is inserted into a slide opening 48 located on the worksurface 38. This automatic slide detection can be accomplished in many ways known to one skilled in the art. For example, when a slide is inserted into a slide opening 48, a camera 70 or other sensor included in the instrument 24 calculates a brightness differential indicative of the presence of a slide and an appropriate signal is registered with the user. When the slide opening 48 is empty, the camera 70 or other sensor reads a first brightness level of the illumination light. When a slide is inserted into a slide opening 48, the camera image sensor or other sensor calculates a second brightness reading wherein the second brightness reading is lower than the first brightness reading and thereby, indicating that a slide has been inserted. Alternatively, when a slide is inserted into a slide opening 48 on the worksurface 38, a light path is blocked by a spring-set flange or by the slide itself indicating the presence or absence of a slide. Upon automatic detection of the slide 12 in the slide opening 48, the camera 70 automatically records a static image of the slide to create a roadmap image and displays it on the visual display unit connected to the computer in a software application window for the static roadmap image.

The handling system 40 is used to bring a carrier 16 with a transfer film 14 affixed to its surface from the cap staging area 50 to the slide location 46 and in juxtaposition to the sample. A software interface window displayed on the visual display unit depicts the worksurface graphic and movement of caps is effected by moving an input device such as a mouse, clicking on a cap and dragging it onto the graphic slide location desired and releasing the mouse button. Software and controllers engage the handling system to effect movement accordingly. The worksurface 38 is automatically moved into the primary optical axis such that a selected opening associated with a slide location 46 or quality control station 54 in the worksurface is aligned with the optical axis and ready for microdissection. The carrier 16 is placed in contact with the sample such that the transfer film contacts the biological material substantially across the entirety of the transfer film surface. Alternatively, the carrier 16 is formed with standoffs 90 such that a substantial portion of the transfer film 14 does not contact the biological material 10 but remains spaced a distance from the sample 10 as shown in step one of FIG. 1. Standoffs are described in U.S. patent application Ser. No. 08/984,979 which is herein incorporated by reference in its entirety. Standoffs are structural features that protrude from the surface of the carrier on the side of the transfer film to provide a spacing between the transfer film and the sample in order to avoid transfer of unwanted friable biological material that would otherwise adhere to the transfer film due to electrostatic forces and the like.

With the sample in the optical axis, the illumination system 36 is activated shedding light on the sample 10. The white light penetrating the sample arrives at the objective 64 and is directed to the acquisition system 70 and/or eyepiece. A live image that is captured by the acquisition system 70 is displayed on the computer monitor 27. Also, a static image of relatively lower magnification is captured so as to provide a roadmap image for navigating the sample space. The two images are displayed side-by-side to locate the user on the sample space map and simultaneously provide a display of the local sample space having a relatively larger magnification. The operator inspects the sample by moving the translation stage via computer inputs, controllers and appropriate software. For example, navigation of the sample space is accomplished by tracing a path on the displayed monitor image using an input cursor via a mouse, joystick or other input means.

Figure 7A:
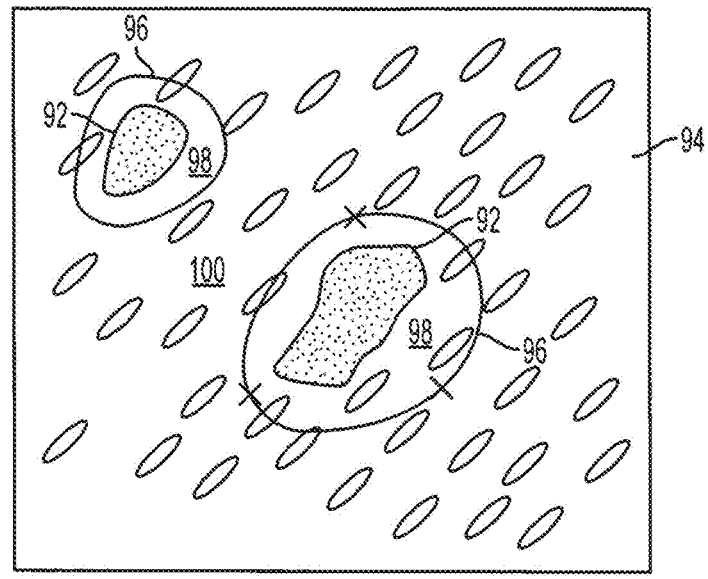
FIG. 7A is a top planar view of a biological sample with targeted portions encompassed by traces according to the invention.

Referring now to FIG. 7, a targeted portion 92 of biological material 94 is identified either manually by the operator or automatically employing software for algorithmic identification of regions of interest. Typically, fluorescent systems are employed for assisting the automated identification of targeted portions of biological material. Manually, the user can trace a targeted portion 92 of biological material viewed on the display monitor by moving a mouse cursor. Each trace 96 defines an interior 98 and an exterior 100. The interior 98 includes the targeted portion(s) and the exterior 100 of the trace includes non-targeted biological material. One or more targeted portions of biological material can be traced and the trace can be of any shape and size as shown in FIG. 7a. Various software microdissection tools for selecting targeted portions of biological material are available. For example, on the software interface, a user selects certain microdissection tools for indicating which cells the capture laser or cutting laser will capture or ablate, respectively, and operate the tools on the live or static image displayed on the computer monitor. Microdissection tools include single point dissection for targeting cells individually, line dissection for drawing a line on the image to target a layer or line of cells, free form dissection for identifying an area to be targeted, and exclusion dissection for deselecting a specific area from targeting. The instrument is optionally selecting for capture only with the capture laser as described with respect to FIG. 1 or ablation with the cutting laser combined with capture with capture laser in a process known as "cut-and-capture".

Figure 7B:
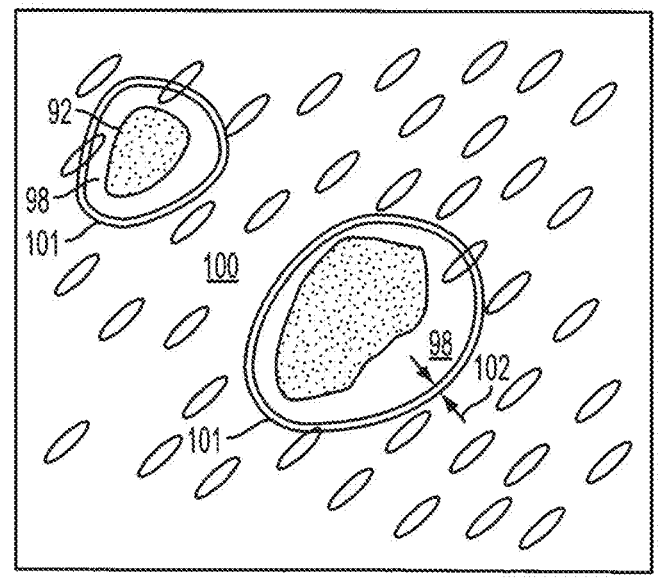
FIG. 7B is a top planar view of a biological sample with targeted portions encompassed by cut paths according to the invention.
Figure 7C:
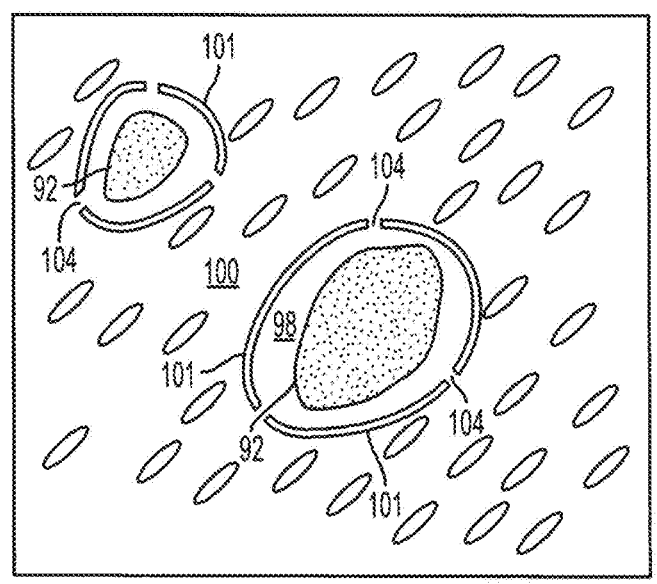
FIG. 7C is a top planar view of a biological sample with targeted portions encompassed by cut paths that are interspersed with bridges according to the invention.

In cut-and-capture mode, the trace defines a cut line for the cutting laser source. After all of the targeted portions 92 have been traced the user is prompted by the computer to commence cutting the traces with the cutting laser source 74. The user may select whether each of the traces are to be closed or substantially closed paths for the cutting laser 74. If the user selects closed paths, the cutting laser source is automatically directed and activated to cut along the traces at a predefined cut width 102 forming a cut path 101 as shown in FIG. 7b. If the user selects a substantially closed path, at least one bridge 104 spanning from the interior 98 to the exterior 100 will be formed such that the interior 98 is joined to the surrounding exterior 100 biological material at the location of the bridge 104 as shown in FIG. 7c. The cut path 101 is interspersed with bridges 104 formed when the UV cutting laser beam is temporarily de-activated while moving along a trace. The bridge width 108 can be selected by the user or predetermined by controlling software. Bridge locations may be user-defined by clicking with the mouse cursor along the trace at locations where bridges are desired as shown by the "x" in FIG. 7a. The user thereby manually selects any number and location of the bridges. Alternatively, the computer may automatically form a predefined number of bridges. The UV laser is activated and the biological material is eroded along the cut path but at bridge locations, biological material remains intact.

During the cutting operation of the UV laser, the laser beam remains stationary and the worksurface 38 serves as a cut line control unit and generates, during the cutting operation, a relative movement between the laser beam and the sample. Alternatively, the cut line control unit comprises a laser scanning device which moves the laser beam relative to the stationary sample during cutting. In such an operation, the worksurface 38 with the sample is not displaced during cutting but remains fixed in the optical axis. The cut line results exclusively from deflection of the laser beam over the sample.

Typically, after the UV laser has cut the biological material along one or more of the trace paths 96, the capture laser 72 is directed at the one or more interiors 98 of the trace paths 96. The IR capture laser 72 is fired or pulsed at an interior 98 to activate the transfer film layer in the location of the interior which then adheres to the interior portion of the biological material. If a carrier with standoffs is being employed, the activated transfer film bridges the distance of the standoffs 90 to contact and adhere to the interior of biological material. An IR laser pulse showing a location of adhesion to the interior of biological material is shown as a circle 106 in FIG. 8a.

Figure 8A:
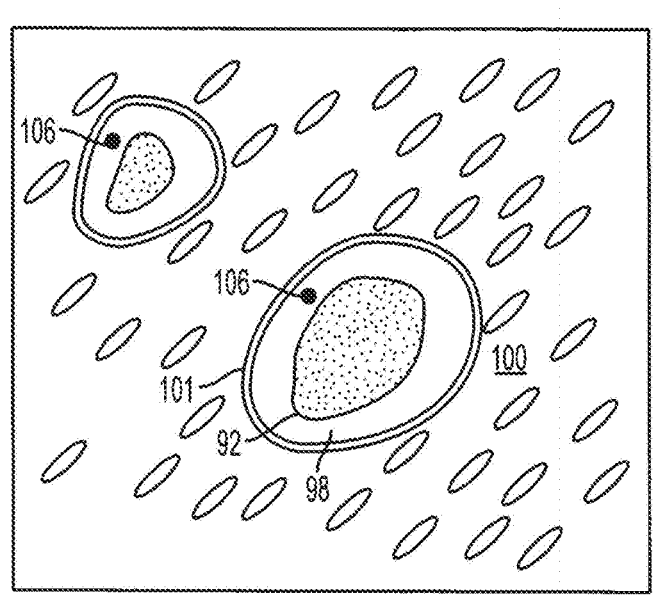
FIG. 8A is a top planar view of a biological sample with capture laser shots located interior of the cut paths according to the invention.
Figure 8B:
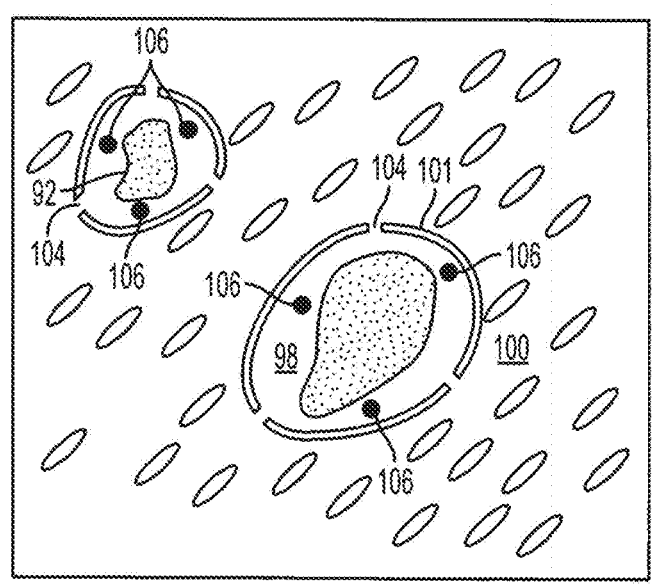
FIG. 8B is a top planar view of a biological sample with capture laser shots located in between the bridges according to the invention.

The IR capture laser 72 can be fired once to create a single area of adhesion or the IR laser can be fired more than once to create more than one area of adhesion on any one interior portion of biological material. The single IR laser shot can be directed in the center of the interior. In another variation, the IR laser shot can be directed at the interior of the trace but at a portion of the interior that was not targeted as desirable biological material as shown in FIG. 8a. In essence, if there is a portion of the interior which contains biological material that is not considered to be a choice selection or otherwise not targeted as desirable, the IR laser can be strategically directed at such a location to advantageously avoid raising the temperature of desired biological material in the area of the IR laser shot which would result from localized heating. If bridges are left by the UV laser trace, IR laser shots shown as circles 106 on FIG. 8b can be directed in-between the bridge locations so that such points of adhesion would assist in the breaking of the bridges when the carrier is lifted away. Also, the IR laser shots can be directed at or in the proximity of the bridge locations.

If the IR laser shots are delivered manually, a user can, for example, click with a mouse cursor at a location where the user desires an IR laser shot to be located. Also, the user may select the number of IR laser shots that are to be made by clicking with a mouse cursor more than once.

If the IR laser shots are delivered automatically, computer software is programmed by the user beforehand or determined automatically to carry out one or more IR laser shots in a uniform or non-uniform pattern of IR laser shots across the interior of a trace. Of course, a single IR laser shot as well as a strategically placed IR laser shot can also be carried out automatically by the computer.

Figure 8C:
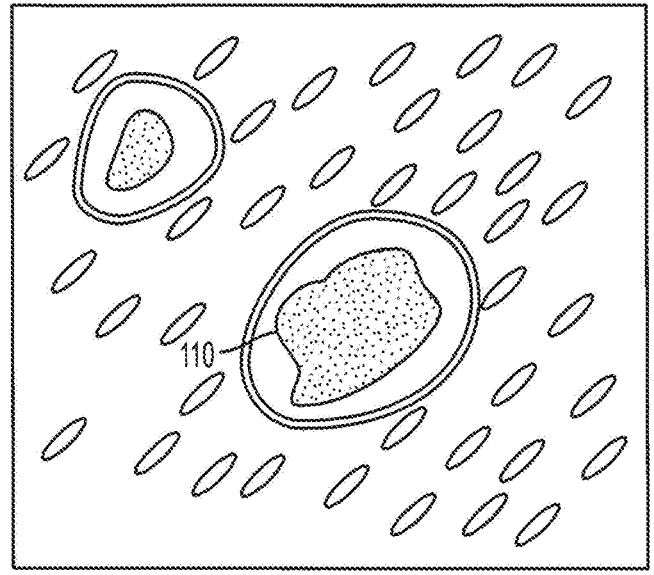
FIG. 8C is a top planar view of a biological sample with an capture laser path that is curved across the interior of a cut path according to the invention.

Furthermore, the IR laser shot is not limited to being a single pulse to create a single point of adhesion. Alternatively, the IR laser can be fired with multiplicity or at duration to trace an IR path 110 of adhesion of any shape within the interior as shown in FIG. 8c. The IR laser path of adhesion is carried out in the same manner as the UV laser path of cutting. Either the worksurface 38 is moved to create a path or the IR laser beam is directed across the interior with the worksurface remaining stationary. Basically, the number of IR laser shots, the shape of the IR laser shots and their location are not limited and any number, pattern, location or shape of IR laser shots is within the scope of the invention. Furthermore, the IR laser shot or shots can be fired before the UV laser is activated to cut the biological material.

Figure 9:
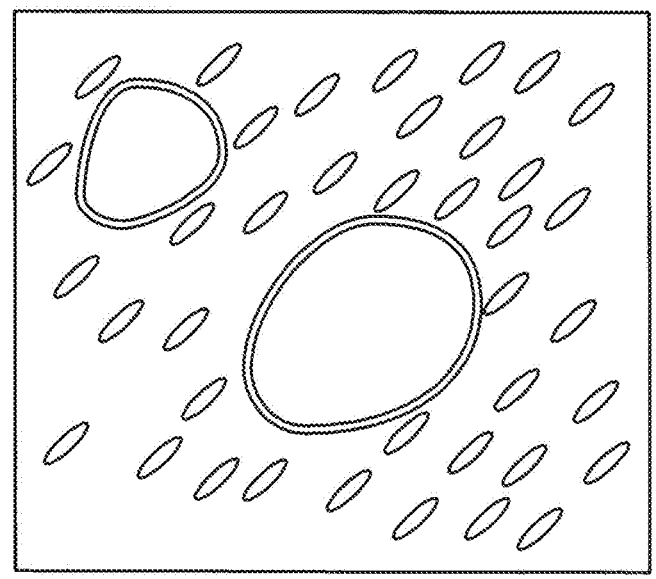
FIG. 9 is a top planar view of a biological sample with targeted portions of biological material removed according to the invention.
Figure 10:
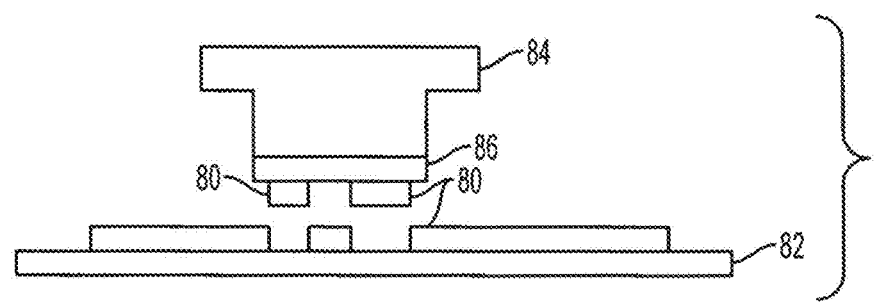
FIG. 10 is a side elevation view of a transfer film carrier with targeted portions adhered thereto and separated from the remaining tissue sample according to the invention.

The carrier with the transfer film will result in one or more areas of adhesion located in the one or more interiors of the cutting laser 74 cut paths. When the carrier is removed by lifting it vertically, the carrier with its attached transfer film and at least one adhered targeted portion of biological material is separated from the remaining layer of biological material. If bridges were formed, those bridges are mechanically broken upon lifting the carrier to free the adhered portions of targeted biological material. What remains is un-targeted biological material as shown in FIGS. 9 and 10. Being adhered to the transfer film, the targeted biological material is removed with the carrier and available for further processing.

If the capture laser 74 shots are delivered automatically and the automatically locate capture laser option is selected in the software, appropriate computer software is programmed to automatically detect the position of the capture laser 74 prior to its activation. Because the capture laser beam can be located anywhere within a predetermined area, it is advantageous to automatically determine the position of the capture laser to provide starting coordinates from which the capture laser beam can be accurately directed to the capture locations. In older instruments, the capture laser is located manually by the user. To manually locate the laser beam, the user moves the worksurface 38 so that a clear laser beam spot appears in the center of the live video window. The user then places the point of the cursor of the computer mouse for example, directly on the center of the laser beam spot and then indicates to the computer that the laser beam has been located by right-clicking on the mouse button and selecting that the location of the laser has been selected. Even in manual capture laser operation, automatically locating the capture laser beam establishes a connection between the cursor and the laser beam so that when the user clicks to fire or target the capture laser, the laser accurately fires on the cells that the user selected.

In the present invention, the instrument 24 automatically locates the capture laser beam without requiring any user intervention. Automatic detection of the capture laser beam is accomplished with appropriate computer software and controllers directing the system to locate the capture laser. First, in one variation, the background illumination such as the white light illuminator 44 is automatically turned off. This step is useful in situations where the capture laser targeting beam is too weak to be seen by the user such as when the capture laser beam is operating in idle mode or if the laser beam intensity is on a low setting. Therefore, it is useful to turn off the background illumination or alternatively, increase the laser beam intensity. In another variation, the laser is set at a level sufficient to be detected by the digital image sensor. This level is generally selected to be below the power level that melts the polymer film. After turning off the background illumination and/or increasing the laser beam intensity, the laser beam spot is detected by the camera as a bright spot relative to the neighboring areas. The exact location of the bright spot and laser beam location is calculated from brightness levels detected by the digital camera image sensor of the acquisition system 70. Given a particular magnification, the pixel coordinates of the beam spot location are translated to planar coordinates for establishing a zeroed location from which the worksurface or the laser beam is precisely directed to areas of interest. Prior to determining the exact location of the laser beam, in one variation, the intensity of the capture laser is increased or fired so that a bright spot is more easily detected. The transfer film is not activated when the laser is fired to locate the beam because the light intensity is set to a low level. After the laser beam is located the background illumination light is turned back on if it was previously turned off. The same procedure described above may be performed for locating the position of the cutting laser. If the cutting laser is activated to indicate a bright spot, it is first directed away from tissue or other desired or sensitive locations to avoid ablation of wanted tissue.

The laser microdissection instrument of the present invention includes an automatic focus feature that automatically focuses the image on the tissue sample being displayed in the live video window. Focusing the tissue sample that is displayed in the live video window involves moving the objective lens 64 in and out until the sharpest possible image of the subject is achieved. Depending on the distance of the subject from the camera, the objective has to be a certain distance from the object tissue to obtain a clear image. The instrument may employ active or passive autofocus techniques that well known in the art. In one variation, an autofocus sensor such as a charge-coupled device (CCD) is included which provides input to algorithms and a microprocessor determines the optimum focus distance for the objective. The instrument automatically focuses on the tissue when a slide is inserted into a slide location and placed in view of the acquisition system.

In addition to autofocus for the image, the laser microdissection instrument of the present invention further includes an automatic focus lock for the capture laser beam that advantageously keeps the capture laser beam focused even after the objective lens is changed or the tissue being observed is varied. The capture laser beam is first focused automatically or manually by moving the beam to an area where there is no tissue or the tissue is very thin and light. The capture laser beam is activated and the coarse and fine focus settings are selected on the software program interface and adjusted until the capture laser beam is a discrete point as viewed in the live image display window. When selected, the coarse and fine focus settings operate to control the laser focus motor. The laser focus motor is connected to the controller and computer and operates to control the focusing lens 62 and adjust the capture laser beam focus. When not in focus, there is a large halo around the center of the capture laser beam and the laser beam spot is blurred. When in focus, the halo around the spot is as close as possible to the focused centroid of the laser beam. In one variation, the capture laser focus setting is recorded as the distance of the laser focusing lens 62 to the focal plane and serves as a baseline from which the focusing lens 62 will be moved to keep the capture laser beam in focus.

Both the objective lens and focusing lens focus on the focal plane of the tissue being observed. When the user navigates across the tissue sample, if necessary, the image is automatically or manually re-focused by automatically or manually moving the objective lens up or down by an objective distance. This objective distance is recorded. If the newly focused region is a region desired for capture, the instrument will prepare for capture by automatically moving the capture laser focusing lens 62 a distance from the focal plane equal to the objective distance that the objective was moved to bring the image into focus in order to keep the capture laser beam set at the desired focus. If the objective lens is moved toward the worksurface on re-focus, the step of automatically keeping the capture laser beam at the desired focus includes moving the laser focusing lens away from the worksurface and if the objective lens is moved away from the worksurface on re-focus, the step of automatically keeping the first laser source at the desired focus includes moving the laser focusing lens toward the worksurface. As the user navigates the tissue specimen and a single objective is used, it may be necessary to refocus the image several times. Each distance that a single objective is moved to focus the image is recorded and summed such that, when ready for capture, the focusing lens can be kept in focus by moving the laser beam focusing lens from the baseline a distance substantially equal to the summed distance that the objective was moved. Alternatively, the focusing lens is moved a substantially equal distance from the focal plane each time the objective lens is moved.

If a different objective lens 64 is selected on the user interface, the computer drives the appropriate motors to turn the objective turret wheel such that the desired objective is positioned in the primary axis. The autofocus system then immediately focuses the image based on the newly selected objective by activating the objective focus motor to move the objective up or down a distance to automatically adjust the foci of the objective which has been positioned and focus the image. However, the focusing lens is kept locked after the new objective is initially focused. This distance that the objective moves to adjust for the newly positioned objective is not recorded and summed together with the other objective distances. However, for any subsequent objective distances that the objective is moved, the focusing lens is moved accordingly, the objective distances being recorded and summed in one variation. Hence, the capture laser is automatically focused such that the focal plane of the capture laser matches the focal plane of the objective lens. If the objective lens is changed, it needs to be refocused. After it is refocused, the focal plane of the capture laser is matched to the focal plane of the new objective.

Because the cutting laser is focused by the objective lens, the cutting laser beam focus is automatically maintained each time the image is focused. If the instrument is arranged such that the cutting laser and the capture laser locations are reversed such that the cutting laser is located above the worksurface and the capture laser is located under the worksurface and the cutting laser is focused by the focusing lens 62 and the capture laser is focused by the objective 64, an automatic focus lock for the cutting laser beam is provided in the same manner as that described above for the capture laser automatic focus lock. It should be noted that in one variation, both the cutting laser and the capture laser are located on the same side of the worksurface and are both focused by the objective lens. In another variation, both the cutting laser and capture laser are located on the same side of the worksurface and are both focused by the focusing lens in accordance with the method described above for the capture laser automatic focus lock.

Figure 11:
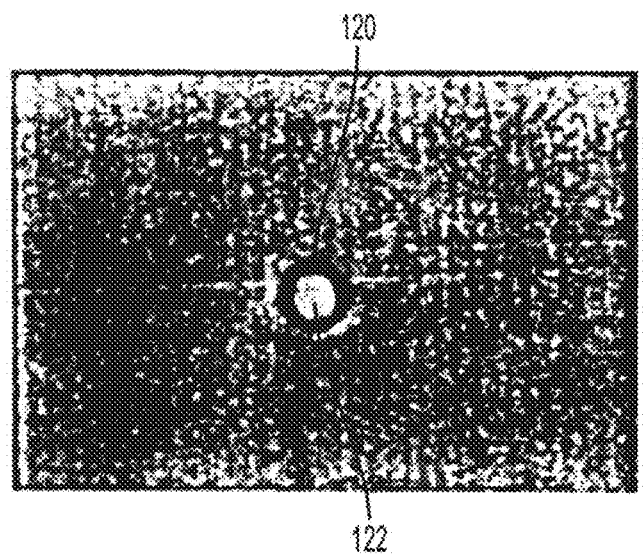
FIG. 11 is a top planar view of an image of a transfer film properly wetted by a capture laser according to the present invention.

Before the capture and cutting lasers are fired, energy levels for each are optimized according to the following methods. To optimize the capture laser setting, the capture laser is fired with the cap in position at an area outside desired tissue where the fired location can be clearly observed by the user. The capture laser is fired and the area is examined for proper wetting. Wetting refers to the melting of the transfer film on the polymer cap so that it fuses adequately to the tissue or cells when the capture laser fires. When the transfer film is visible as a dark ring 120 fused to the slide and the center 122 of the ring is clear, the wetting is adequate as shown in FIG. 11. If the wetting is not adequate, one or more capture laser parameters such as power and duration are adjusted. In one variation, the power setting of the capture laser is increased if the wetting is not adequate. In another variation, the duration of the capture laser is increased. The capture laser beam is directed at an adjacent location and test fired again at the higher power and/or duration setting. The area is observed to determine whether wetting is adequate. If not, the process is repeated with the power setting or duration being increased incrementally. Determination of whether wetting is adequate may be accomplished manually by the user via observation or automatically by the instrument employing various algorithms. In an automated variation, the acquisition system camera image sensor records intensity data for an image of each test fire location. The microprocessor looks at the difference in intensity among the adjacent pixels and detects a maximum intensity difference between adjacent pixels that correspond to a dark ring to determine the optimum energy setting.

Figure 12:
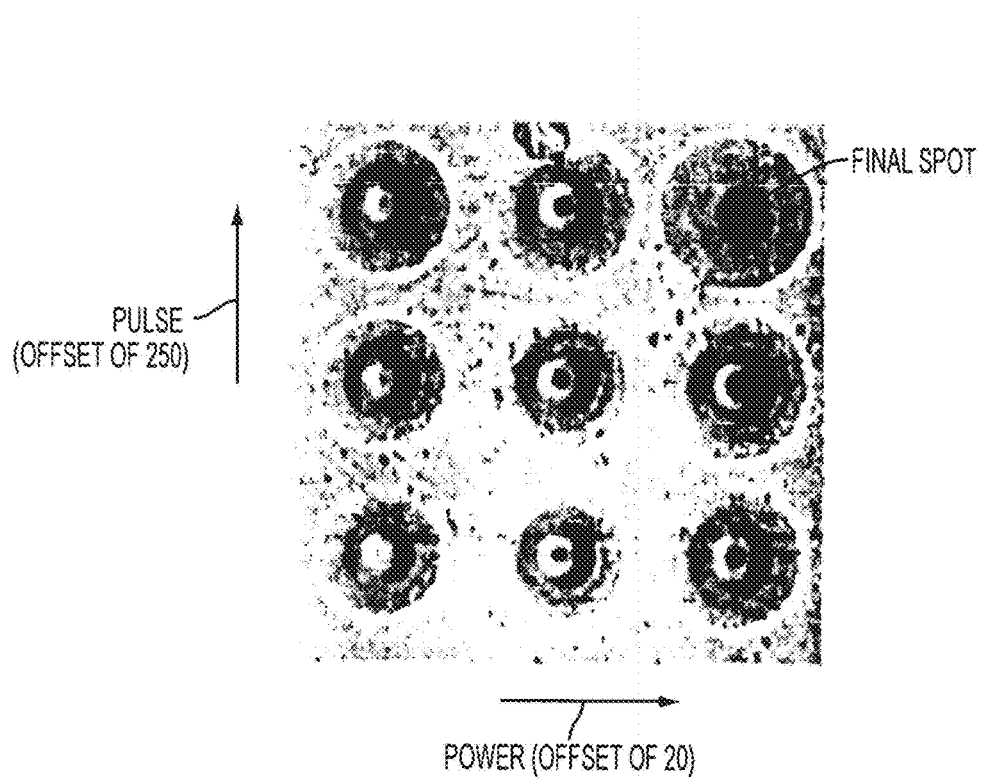
FIG. 12 is a top planar view of an image of a calibration matrix of capture laser spots according to the present invention.

Referring now to FIG. 12, in one variation, a calibration matrix is used to determine capture laser settings. The laser matrix option allows the user to set up a test firing pattern to determine the appropriate settings for the capture laser to adequately wet the film. For one axis of the matrix, the user enters the number of steps for power increments, the power increment per step, and the distance between laser spots. For another axis of the matrix, the user enters the number of steps for duration increments, the duration increment per step, and the distance between laser spots. The computer automatically fires the capture laser test pattern according to the settings to create a matrix as shown in FIG. 12. The user then observes the pattern and selects the optimum power and duration settings for the capture laser as desired.

To optimize the cutting laser setting, the cutting laser is fired at an area of tissue and the area is examined for a proper tissue burn spot. A tissue burn spot typically appears white in color. If there is no burn spot detected on the tissue, one or more cutting laser parameters such as power and duration are adjusted. In one variation, the power setting of the cutting laser is increased if the burn is not adequate. In another variation, the duration of the cutting laser is increased. The cutting laser beam is directed at an adjacent location and test fired again at the higher power and/or duration setting. The area is observed to determine whether burn sport is adequate. If not, the process is repeated with the power setting or duration being increased incrementally. Determination of whether the burn spot is adequate is typically accomplished manually by the user via observation.

In one variation, a calibration matrix is used to determine cutting laser settings as described above with respect to the capture laser calibration matrix and FIG. 12. The laser matrix option allows the user to set up a test firing pattern to determine the appropriate settings for the cutting laser to adequately cut the film. For one axis of the matrix, the user enters the number of steps for power increments, the power increment per step, and the distance between laser spots. For another axis of the matrix, the user enters the number of steps for duration increments, the duration increment per step, and the distance between cutting laser spots. The computer automatically fires the cutting laser test pattern according to the settings to create a matrix similar to that shown in FIG. 12 for the capture laser. The user then observes the pattern and selects the optimum power and duration settings for the cutting laser as desired.

As described above, the instrument includes a worksurface 38 that includes at least one cap quality control station 54. The quality control station 54 is one or more than one location on the worksurface designed for viewing the captured tissue after microdissection. The worksurface 38 at the location of the quality control station includes an opening such that when a cap is placed in the quality control station, illumination or laser light passes through the opening and through the cap. The captured tissue adhered to the transfer film on the cap is illuminated for observation or exposed to the capture laser or cutting laser for ablation.

After capture in the slide location 46, transferred tissue is attached to the cap and carried along therewith and placed in the quality control station 54. It should be noted that capture in the slide location is by any one or more of the methods described in U.S. Provisional Patent Application Ser. No. 60/613,038, entitled "Automated microdissection instrument" filed on Sep. 25, 2004; U.S. patent application Ser. No. 10/989,206 entitled "Automated laser capture microdissection" filed on Nov. 15, 2004; U.S. patent application Ser. No. 11/222,281 entitled "Laser microdissection apparatus and method" filed on Sep. 8, 2005; and U.S. patent application Ser. No. 10/982,230 entitled "Laser microdissection on inverted polymer films" filed on Nov. 4, 2004 all of which are incorporated herein by reference in their entirety and also a single cap can be used to collect material from more than one tissue slide, prior to being placed in the quality control station where further observation and exposure to the cutting laser and/or capture laser is optional. For example, the sample undergoes laser capture microdissection with a capture laser while in the slide location prior to being placed in the quality control station where it is further observed and exposed to the cutting laser and/or capture laser. In another example, the sample undergoes microdissection with a cutting laser and is exposed to the capture laser prior to being placed in the quality control station where it is further observed and exposed to the cutting laser and/or capture laser. Following cell capture in the slide location, the user inspects the slide and the cap in the quality control station to verify that collection was successful. In the quality control station, the camera captures a static or live image of the cap transfer surface including the accompanying captured tissue and displays it on the computer monitor. The image is displayed either on the live video window or the static image window of the computer software interface, and the user inspects the quality of the capture. If there is undesirable friable tissue or other matter still attached or capture is incomplete or unsatisfactory, undesirable portions of the tissue can be targeted for ablation with the cutting laser while the cap is located in the quality control station and/or targeted for laser capture with the capture laser while the cap is located in the quality control station. Photoablation, the volitization of tissue by light emitted from an ultraviolet cutting laser, while the cap is in the quality control station is performed interactively. The user ablates any unwanted tissue from the material on the cap. There are two modes for ablating. In the first mode, the user turns on the cutting laser and moves the mouse cursor over the region to ablate. When finished, the user turns off the cutting laser. In the second mode, user holds one or more hot keys such as the CONTROL and SHIFT keys at the same time and moves the mouse cursor to move the laser. The cutting laser fires only while the keys are depressed and when released, the laser turns off. When inspection and microdissection is completed in the quality control station, the user points the mouse cursor on the cap depicted on the software interface residing in the quality control station and directs the cursor to move the cap from the quality control station to the unload station 52.

Referring back to FIG. 4, a new cap, when introduced into the laser microdissection instrument, is located in the staging area 50 of the worksurface 38. From the staging area 50, the cap is placed on a slide located in any one or more slide locations 46 on the worksurface. From a particular slide location, after microdissection for example, the cap may be moved to the quality control station or directly to a particular location on the unload station 52. Once the cap is moved from a particular slide in the slide location, the cap is disassociated from its identifying slide and tissue information. It is desirable to identify which slide or tissue sample a cap or microdissected region is associated with or from. To accomplish this identification, each cap is tracked by recording one or more tracking information and associating that tracking information with each cap. A tracking information is any useful identification information that is associated with a particular cap. For example, the tracking information may include a cap number, cap style, project number, or any other information. An example of a cap number or identification is the cap's location in the cap station. For example, if the cap is first in the cap station it may be assigned a tracking information of "CAP #1". Additional information or notes may be associated with this identification including date and time of microdissection for example, and the style of cap that is used such as the CapSure™ HS or CapSure™ Macro. When a cap is moved from the cap staging area 50 and into the slide location 46, it is placed on one tissue-bearing slide in a particular slide opening 48. At this point, another tracking information is recorded and associated with CAP #1. An example of such a tracking information is "SLIDE #3" to identify the tissue-bearing slide in a slide opening 48 on the slide location 46 on which the cap was placed. "SLIDE #3" for example designates the third slide opening 48 in the slide location 46. Additional information associated with a particular slide that has been entered by the user or automatically recorded such as the slide name, tissue type, number of captures, total area of captures and special notes and type of slide or any other useful or important information that is associated with "SLIDE #3" is also recorded with the other previously-recorded tracking informations. From the slide station, the cap may be moved to the quality control station 54 and an additional tracking information such as "QC" may be recorded and associated with the cap. If additional ablation takes place at the quality control station, that information is also recorded and associated with the particular cap. From the quality control station, the cap is moved into the unload station 52 and positioned in a particular location on the unload station and another tracking information, such as the coordinates of the cap location on the unload station, "X1,Y1", is recorded and associated with the cap. In general, as the cap is put through the steps of a prescribed procedure, a tracking information is assigned, recorded and associated with the cap. Hence, if a user wishes to track the cap it requests the tracking information on the user interface and a list of tracking informations or codes associated with the cap process is outputted. For example, a tracking report may include a string of tracking codes such as "CAP#1" "SLIDE#3" "EPITHELIAL" "QC" "X1,Y1". Such a tracking report informs the user that the captures on CAP #1 came from tissue sample on SLIDE#3. Additional tracking information that may be associated with a particular cap include a roadmap image of the slide from which tissue was captured, an information associated with a reading of a barcode located on the slide from which tissue was captured or a picture of the barcode itself. The tracking information is recorded and associated with the first substrate or cap linking the first substrate or cap, the biological material, and the at least one second substrate or tissue slide(s) from which the biological material was removed. It should be noted that a single cap can be used to collect material from more than one slide.

Alternative methods of tracking information associated with a cap include burning a tracking code or other identified with a laser such as the UV cutting laser onto the cap itself or onto the transfer film with the IR capture laser in dot matrix format for example to script the information. Another method includes simply associating the static roadmap image of at least a portion of the slide with the particular cap such that the tracking information outputs the associated roadmap image. Yet another method includes, reading a slide label information such as a barcode, alpha-numeric text or other characters, and recording the slide label information associated with the cap. In one variation, the slide label information is converted and the converted data is associated with the cap. For example, a bar code is read and converted into text data for example and the text data is recorded and associated with the cap. Another example includes optical character recognition of characters on the slide which is then reproduced, recorded and associated with a cap. Of course, a camera of the acquisition system can be used to capture slide information and the image itself can be associated with the cap or data can be deciphered from the image in another variation.

All publications and patent applications mentioned in this specification are incorporated herein by reference to the same extent as if each individual publication or patent application were specifically and individually indicated to be incorporated by reference.

The above description is illustrative and not restrictive. Many variations will be apparent to those skilled in the art upon review of this disclosure. The scope of the invention should not be determined with reference to the above description, but instead should be determined with reference to the appended claims and the full scope of their equivalents.

What is claimed is:

1. A method for automatically determining the location of a laser beam projection on a worksurface area of a laser microdissection instrument that is operatively coupled to a microprocessing device and a digital image acquisition system containing a digital image sensor, the method comprising the steps of:

emitting a laser beam from a laser used in a cut-and-capture microdissection of a biological sample at an intensity at a level sufficient to be detected by the digital image sensor;

detecting the sufficient light intensity of the laser beam by the digital image sensor;

determining the pixel location of the laser beam on the digital image sensor;

converting the pixel location of the laser beam on the digital image sensor to a coordinate location corresponding to the worksurface area; and assigning the coordinate location to the location of the laser beam, wherein the coordinate location establishes a zeroed location.

2. The method of claim 1, wherein detecting a sufficient light intensity of the laser beam includes turning off background illumination.

3. The method of claim 1 further including, controlling the movement of the laser beam relative to the worksurface from the assigned zeroed coordinate location to a target location of an area of interest of a biological sample.

4. The method of claim 1, wherein detecting a sufficient light intensity of the laser beam includes increasing the intensity of the laser beam.

* * * * *